United States Patent [19]
Art

[11] Patent Number: 5,954,924
[45] Date of Patent: Sep. 21, 1999

[54] DISTILLATION OF VINYLAROMATIC MONOMER

[75] Inventor: Billie E. Art, Sulphur, La.

[73] Assignee: Yield Improvement Engineering, Inc., Baton Rouge, La.

[21] Appl. No.: 08/537,125

[22] Filed: Sep. 29, 1995

[51] Int. Cl.[6] ...................................................... B01D 3/42
[52] U.S. Cl. ......................... 203/1; 203/4; 203/7; 203/9; 203/DIG. 6; 202/154; 585/5; 585/800
[58] Field of Search .................................. 203/1, 2, 4, 7, 203/8, 9, 99, 69, DIG. 6; 202/154; 585/5, 800, 806, 807

[56] References Cited

U.S. PATENT DOCUMENTS

| | | | |
|---|---|---|---|
| 3,904,484 | 9/1975 | King | 203/52 |
| 3,988,212 | 10/1976 | Watson | 203/9 |
| 4,033,829 | 7/1977 | Higgins, Jr. et al. | 203/9 |
| 4,061,545 | 12/1977 | Watson | 203/9 |
| 4,105,506 | 8/1978 | Watson | 203/9 |
| 4,177,110 | 12/1979 | Watson | 203/9 |
| 4,191,614 | 3/1980 | Watson et al. | 202/177 |
| 4,272,344 | 6/1981 | Watson | 202/154 |
| 4,468,343 | 8/1984 | Butler et al. | 252/403 |
| 4,469,558 | 9/1984 | Watson | 202/154 |
| 4,615,769 | 10/1986 | Horigome et al. | 203/2 |
| 4,623,431 | 11/1986 | Kendall et al. | 203/9 |
| 5,386,075 | 1/1995 | Keil et al. | 585/800 |

*Primary Examiner*—Christopher Kim
*Attorney, Agent, or Firm*—John F. Sieberth; R. Andrew Patty, II

[57] ABSTRACT

Process technology is described making possible substantial improvements in the separation and recovery of highly pure vinyl aromatic monomers, notably styrene. A number of design, construction and operational features are made available for selection and use both for new plant facilities and for upgrading existing plant facilities. One major aspect of the invention is reduction in retention or residence times in the distillation towers.

64 Claims, 12 Drawing Sheets

STYRENE DISTILLATION - ONE PREFERRED CONFIGURATION

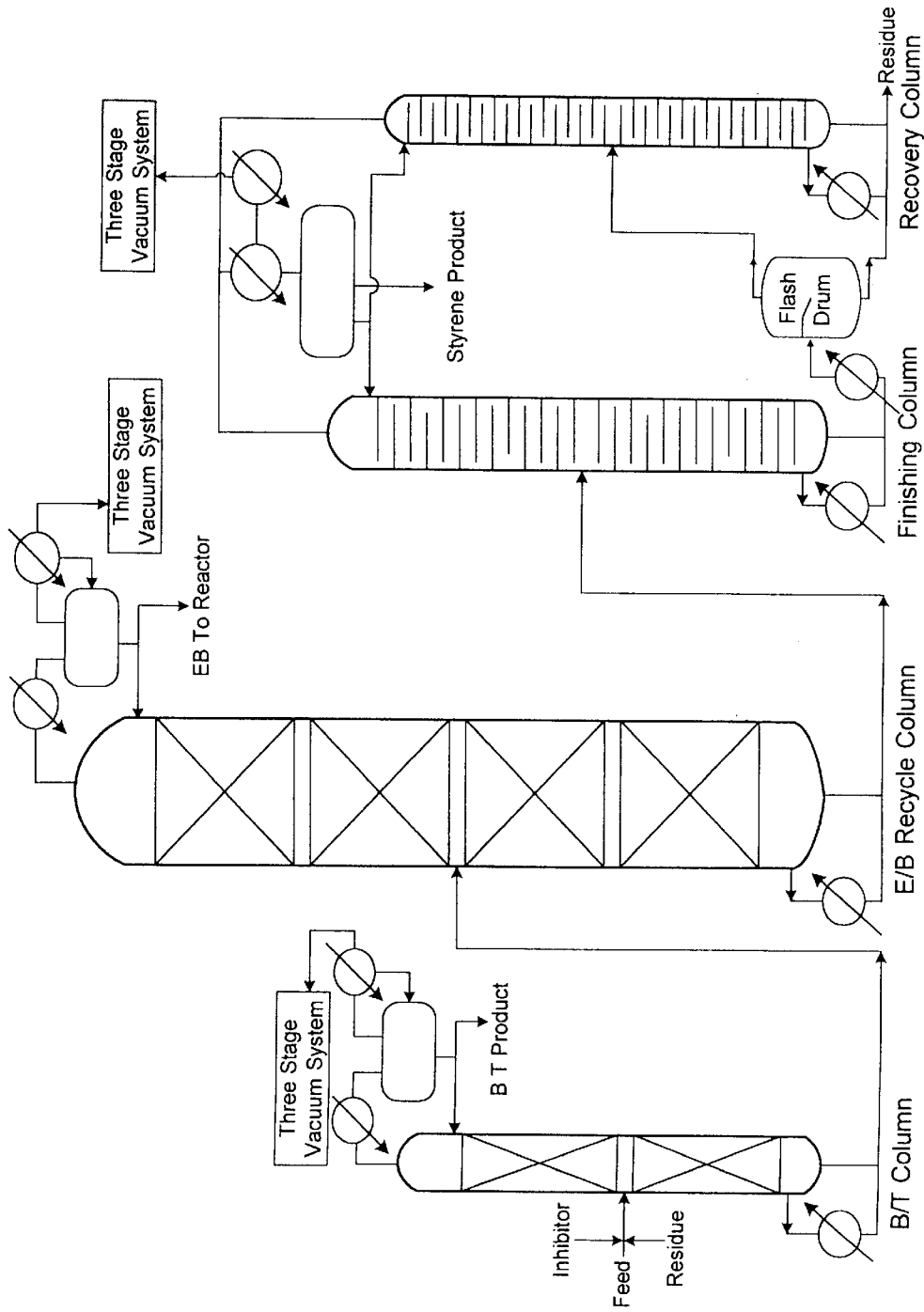
FIGURE 1 – STYRENE DISTILLATION – ONE CURRENT CONFIGURATION

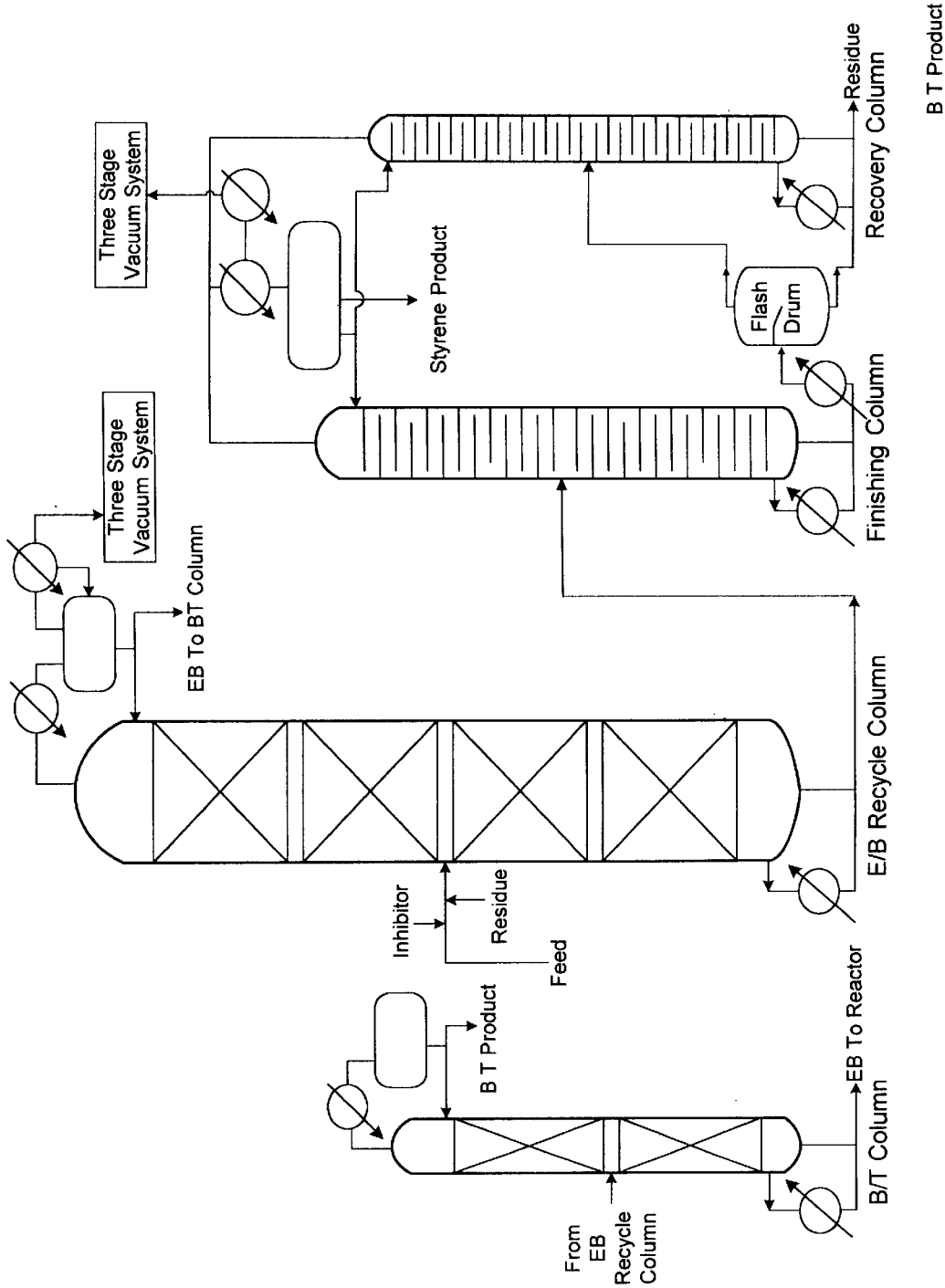
FIGURE 2 - STYRENE DISTILLATION - ANOTHER CURRENT CONFIGURATION

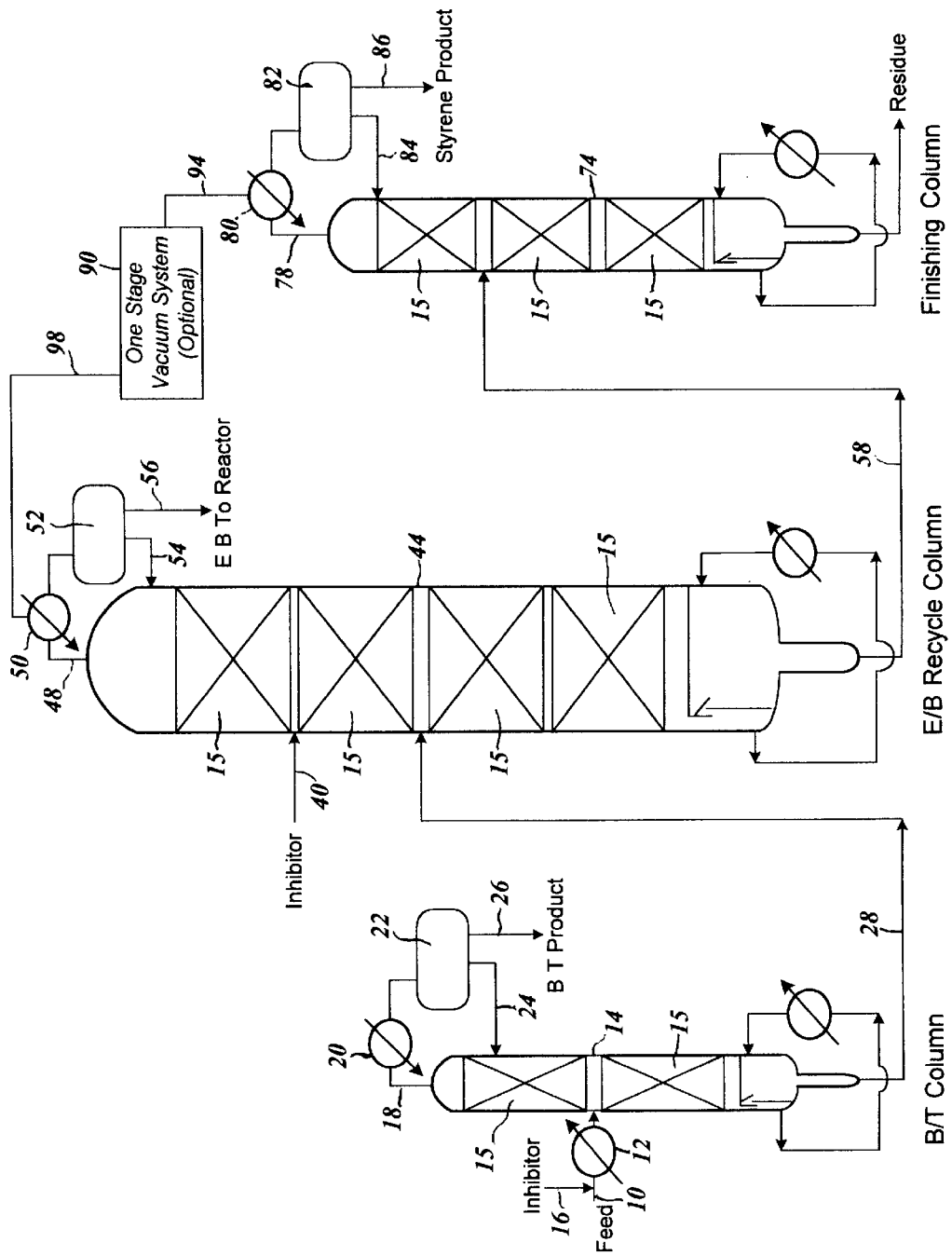
FIGURE 3 - STYRENE DISTILLATION - ONE PREFERRED CONFIGURATION

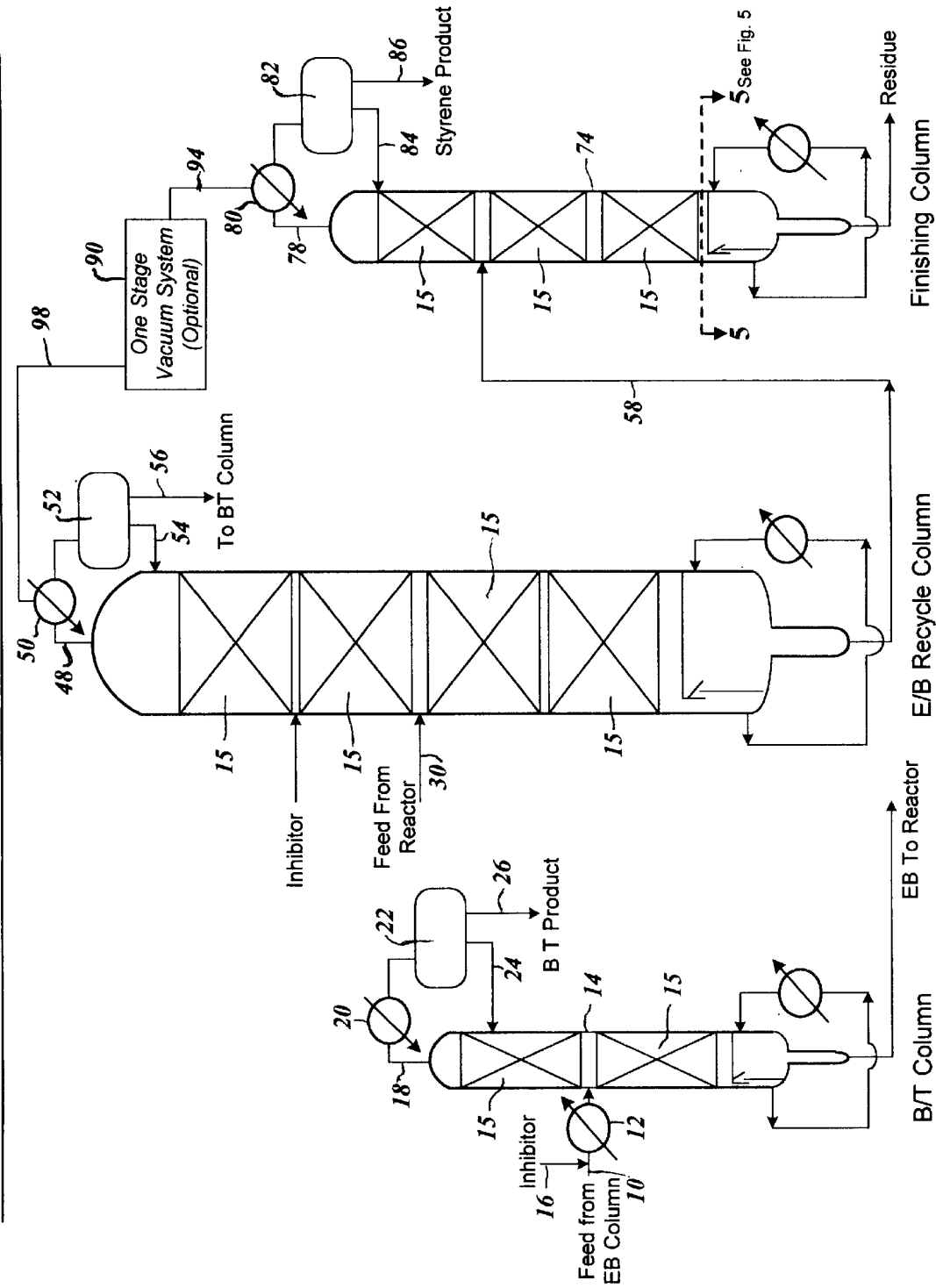
FIGURE 4 - STYRENE DISTILLATION - ANOTHER PREFERRED CONFIGURATION

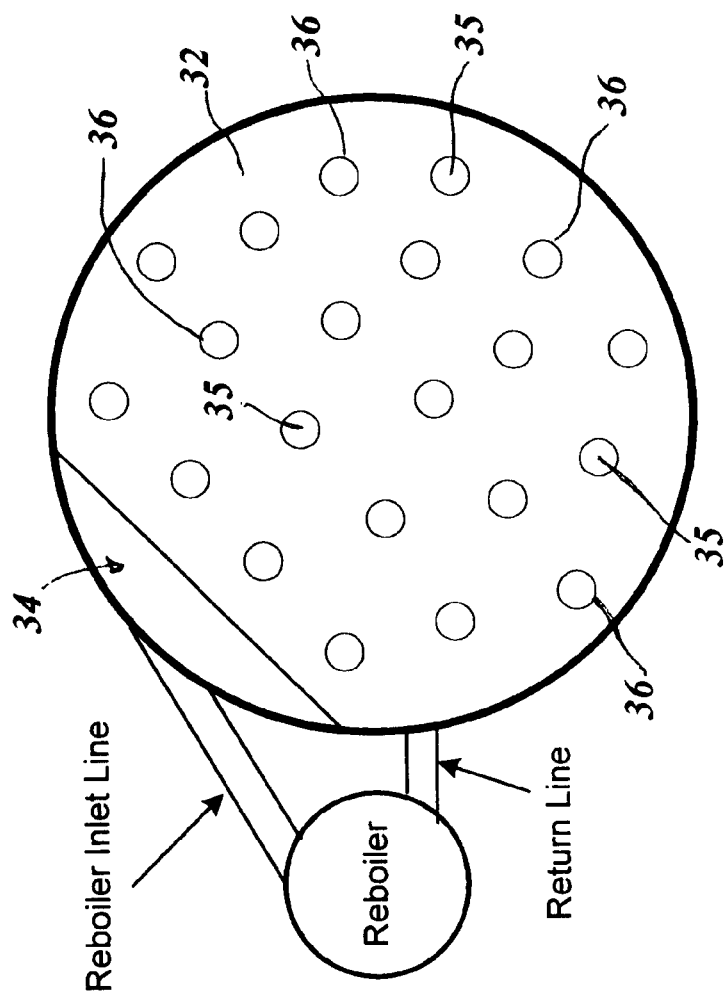
FIGURE 5 - TOWER BOTTOM MODIFICATIONS (Top View)

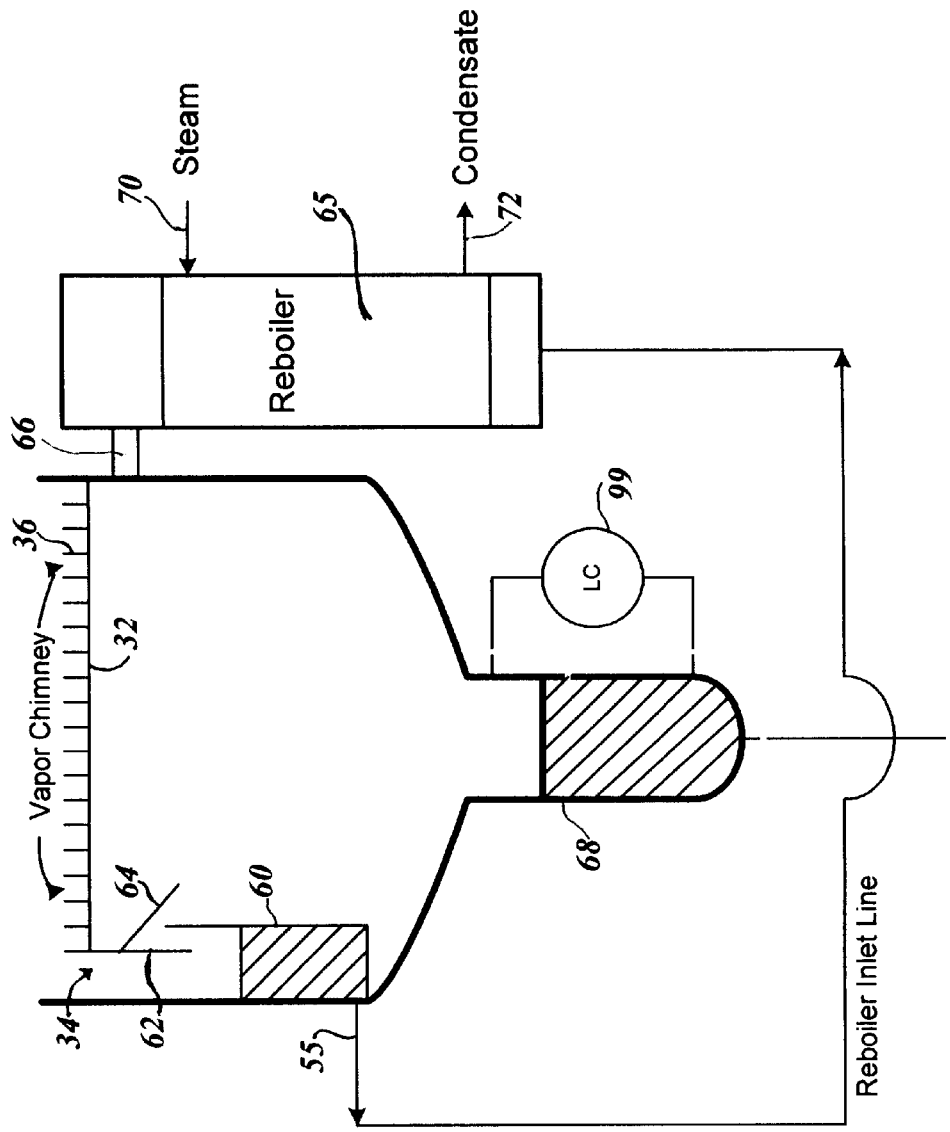
FIGURE 6 - TOWER BOTTOM MODIFICATIONS (Side View)

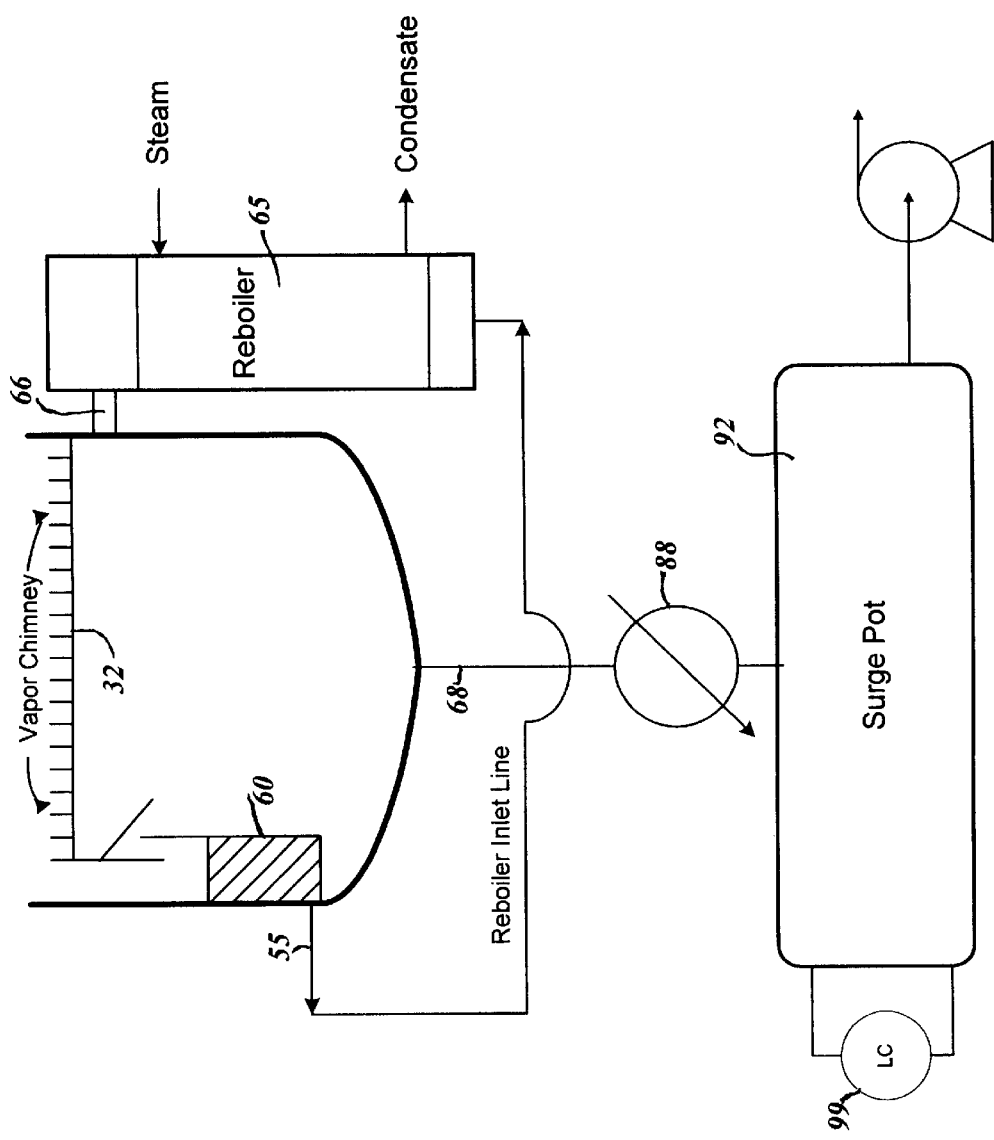
FIGURE 7 - OPTIONAL BOTTOM COOLER FOR EB AND BT COLUMNS

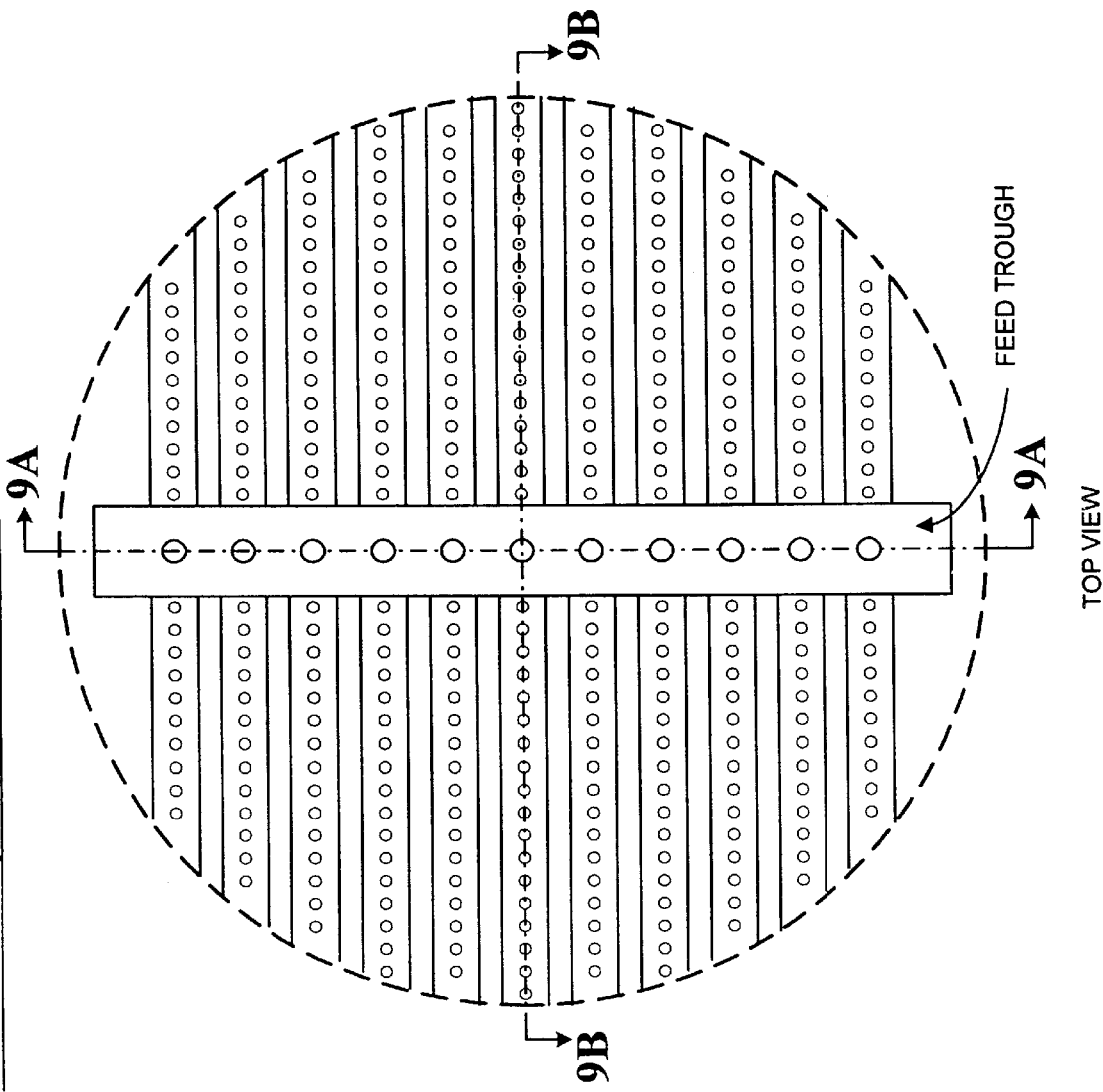
FIGURE 8 - LIQUID TROUGH DISTRIBUTOR/REDISTRIBUTOR (Top View)

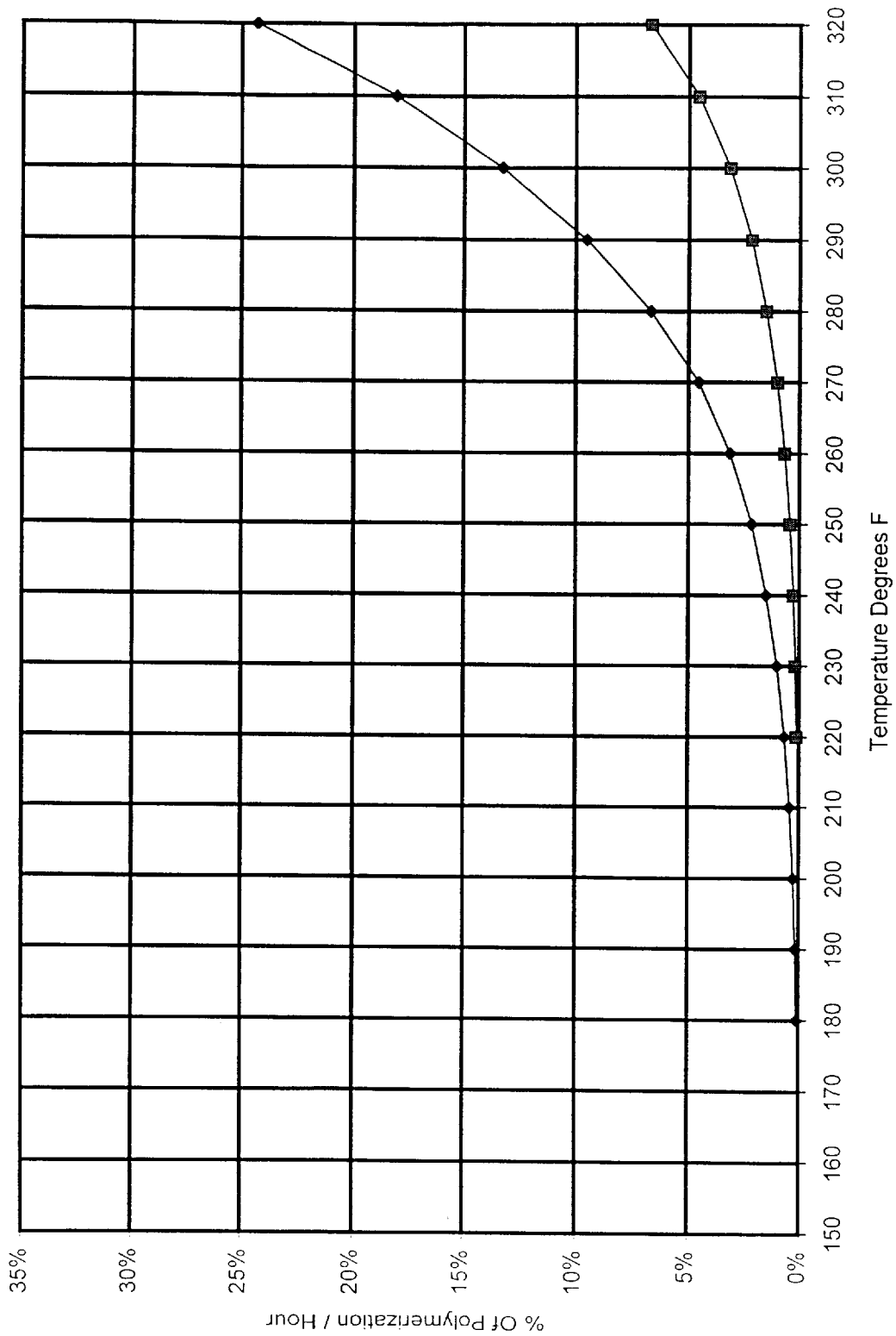

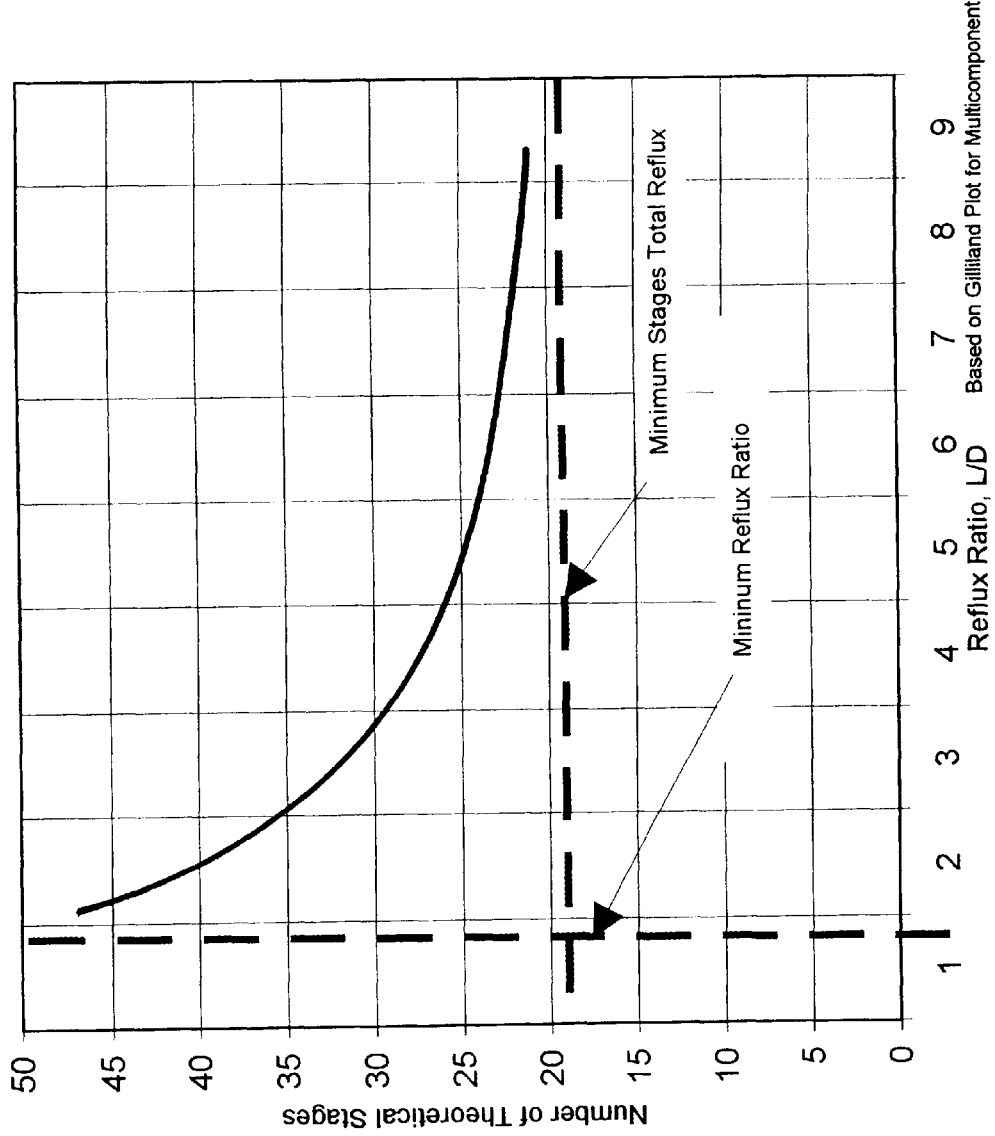

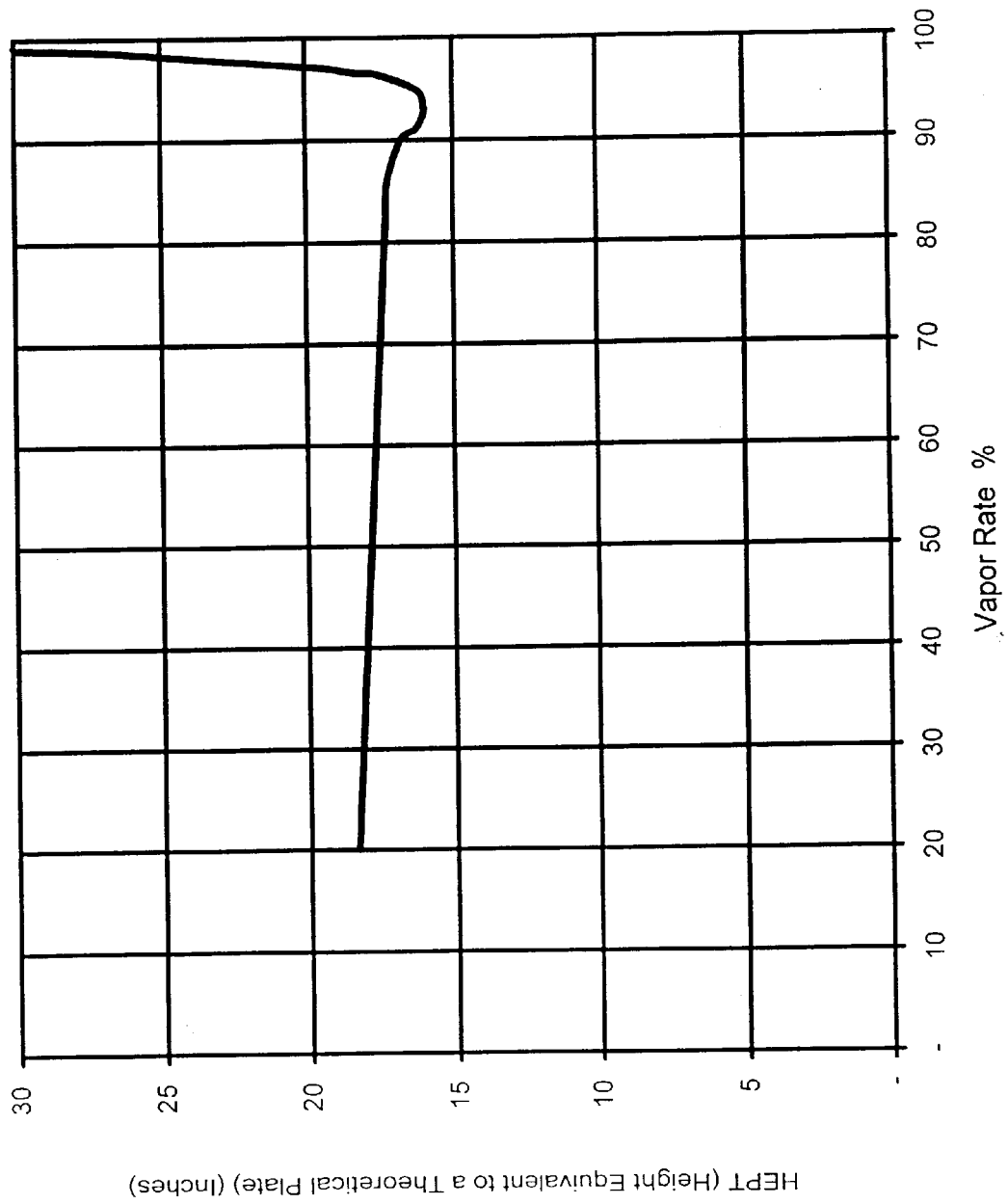

DISTILLATION OF VINYLAROMATIC MONOMER

TECHNICAL FIELD

This invention relates to improvements in the art of distilling mixtures containing vinylaromatic monomers, especially mixtures containing styrene monomer.

BACKGROUND

To facilitate discussion, much of the ensuing description will largely be with reference to styrene production and purification. However, similar principles and considerations apply in the case of other analogous vinylaromatic monomers.

Styrene monomer is usually produced commercially by the dehydrogenation of ethylbenzene in a vapor phase, fixed catalyst-bed reactor. Each pass through the reactor converts about 60 to 70% of the ethylbenzene to styrene. Certain impurities are produced in the styrene reactor—mainly, benzene and toluene. Other impurities are present in the incoming ethylbenzene feed. These are mainly xylenes, cumene, α-methylstyrene, and polyethylbenzenes.

Distillation is used to purify the styrene monomer to customer specifications (usually 99.9+wt %). The ethylbenzene is removed for recycle to the styrene reactor. Benzene is recycled to the Ethylbenzene Unit in which ethylbenzene is produced by ethylation of benzene.

Toluene is recovered as a saleble product. The other impurities are used as fuel for the process. Typically a styrene plant will use one of two commercially available distillation configurations such as illustrated in FIGS. 1 and 2. The primary differences in the two systems is whether the fresh feed is introduced into the BT Column or into the EB Recycle Column.

The styrene monomer is a reactive chemical used to produce a wide range of polymers and rubbers. This reactivity makes distillation of styrene monomer difficult because the styrene tends to polymerize in the distillation column. Any styrene monomer which polymerizes will be removed with the heavies and used as fuel. This polymerization represents a serious economic penalty when valuable product styrene is converted to a waste fuel. If the polymerization reaction goes too far, the distillation system may become fouled with polymer thereby decreasing efficiency, or may even plug completely with hard polymers thereby damaging equipment. Since the rate of styrene polymerization increases with increase in temperature, conventional practice involves operating the distillation columns of commercial styrene plants at low pressures to reduce boiling temperatures and thereby reduce the extent of adverse polymerization. Table 1 shows typical temperatures and pressures of a modern styrene plant.

TABLE 1

Styrene Distillation Pressure and Temperature Relationships

| Distillation Column | Column Portion | Pressure, psia | Temperature, Degrees F. |
|---|---|---|---|
| BT Column | Top | 4.0000 | 145 |
|  | Bottom | 4.5029 | 207 |
| EB Recycle | Top | 1.4500 | 162 |
|  | Bottom | 2.9780 | 206 |
| Styrene Finishing | Top | 1.1000 | 159 |
|  | Bottom | 1.2159 | 192 |

TABLE 1-continued

Styrene Distillation Pressure and Temperature Relationships

| Distillation Column | Column Portion | Pressure, psia | Temperature, Degrees F. |
|---|---|---|---|
| Styrene Recovery | Top | 2.5145 | 159 |
|  | Bottom | 3.9458 | 289 |

In addition to temperature control, another method is used to reduce polymerization. So far as is known, all commercial plants add a polymerization inhibitor to the styrene distillation train. The polymerization inhibitor shifts the polymerization rate curve to higher temperatures and thus reduces the amount of polymerization occurring at operating temperatures. A number of inhibitors are available with varying degrees of effectiveness.

Since the primary defense against polymerization is distillation at reduced temperature achieved by use of low pressure (vacuum), standard commercial practice is to operate styrene plants at as low a pressure and temperature as possible. Vacuum distillation columns are usually very large. The largest column in any styrene plant is the Ethylbenzene (EB) Recycle Column. Typically, this column is close to 200 feet high and 16 to 36 feet in diameter.

A number of factors have been used in arriving at the size and type of columns installed in a commercial styrene distillation facility. One factor is column height. A distillation column is designed to separate chemicals by repeated boiling and condensing of the chemical mixture. The lighter or lower boiling point temperature chemicals will concentrate in the vapor and leave the column overhead and the heavier chemicals will concentrate in the liquid and leave the column bottom. The closer together the boiling point of the chemicals to be separated, the more difficult is the separation. The measurement of this degree of separability is called relative volatility. Higher relative volatility means easier separation.

Ethylbenzene and styrene have close boiling points. This means the mixture must be boiled and condensed many times to achieve a separation. The amount of separation achieved if the mixture was heated one time and allowed to reach equilibrium between the vapor and the liquid is called one theoretical stage.

In a distillation column, vapor and liquid phases flow countercurrently. The column is fitted with trays or packing to maximize the contact between the two phases. At the bottom of the column, the liquid mixture is heated to send vapor up through the column. At the top of the column, vapor is condensed and sent back down the column as liquid. The liquid sent back to the top of the column is called reflux. The term "reflux ratio" is usually defined as the quantity of liquid returned to the column divided by the amount of liquid product taken from the overhead. The number of theoretical stages required for any given separation of a mixture of two or more chemicals is a function of reflux ratio. FIG. 11 is the Gilliland correlation which demonstrates this relationship of theoretical stages to reflux ratio. The curve for any given separation is asymptotic on one axis to the minimum number of stages at total reflux, and on the other axis to the minimum reflux required at an infinite number of stages. Therefore by setting a reflux ratio, the number of theoretical trays required in a distillation column may be determined. In the actual column, the number of stages determines the number of trays required in a tray column or the height of packing needed in a packed column.

The number of trays or packing height in turn sets the column height. Consequently, the height of a distillation column may be determined at least in part by defining the separation required and the reflux ratio to be employed.

Another factor used in arriving at column size and type is column diameter. The diameter of a distillation column is determined by internal flow rates of liquid and vapors. Vacuum distillation towers are sized for the vapor volumetric flow rate ($ft^3$/hr or $m^3$/sec). Liquid rates typically do not determine vacuum tower diameter. At maximum vapor loading for any distillation column, liquid begins to be entrained in the vapor. If the vapor rate is increased, the liquid will not be able to flow freely through the column and the column will fill with liquid. This condition is called flooding.

Reflux ratio affects the vapor loading. Every pound of liquid sent back to the column as reflux must first have traveled through the tower and out the overhead as a vapor. Therefore, higher reflux results in higher vapor loading.

In designing a distillation column, a decision must be made whether to invest in tower height or in tower diameter. Operation at the minimum reflux ratio would allow the minimum vapor flow through a column and, therefore, the minimum column diameter. At the minimum reflux ratio the tower must be infinitely tall to make the given separation. Obviously the tower must be designed with a higher than minimum reflux ratio to reduce the tower height to a practical size. In the case of a high capacity vacuum tower, such as those used in the usual current styrene process, the practical limit for tower diameters is being approached. To minimize the diameter, reflux ratios near the minimum are being used.

Still another factor tending strongly to increase column size is large plant capacity and throughput. In practice, large diameter vacuum columns are required in styrene distillation facilities in order to process the large capacity of modern plants and maintain operating temperatures low enough to limit styrene polymerization to an acceptable level. However, these large diameter vacuum towers have certain problems inherent with their size.

Most new plants use structural packing in the B/T column and EB Recycle Column. A few have installed structural packing in the Styrene Recovery Column (not to be confused with the finishing column employed in preferred embodiments of this invention described hereinafter). Structural packing has a much lower pressure drop per theoretical stage than a trayed column. Since the pressure drop across the total column is lower, the pressure on the bottom of the column (maximum pressure location) is lower. A lower bottom pressure creates a lower bottom temperature and; therefore, results in less polymerization.

Sizing a structural packing vacuum column requires consideration of another factor, viz., minimum liquid loading. Structural packing requires a minimum liquid loading in gallons per minute or pounds of liquid per hour for each square foot of packing cross sectional area. It is possible to increase liquid flow by increasing reflux. However, as previously discussed, this also increases the vapor flow, which requires an increase in diameter, thus creating additional cross sectional area, and further reducing the liquid loading per square foot thereby defeating the purpose of the reflux increase. Typically the liquid loading in the Styrene Finishing Column is so low that structural packing is not used.

Historically, large diameter packed columns with low liquid loads are inefficient. Poor liquid distribution and also dry areas of packing result in lost efficiency. A recent analysis of an EB Recycle Column showed a 24% loss (from design) of efficiency. Efficiency drops as tower diameter increases and as liquid loading decreases in all packed columns per Klemas and Bonilla, *Chemical Engineering Progress*, July 1995, PP 27–44.

Styrene distillation towers using current technology are not very rate flexible. Rates may not be significantly increased due to maximum vapor flow, or be significantly decreased due to minimum liquid loading. Rates may be decreased by loading the tower with extra reflux to compensate for the reduction in product. However, this practice produces higher per pound energy costs.

Styrene towers are difficult and expensive to construct. A worldscale EB Recycle Column must be field constructed, a costly and time-consuming process. The EB Recycle Column is typically the single most expensive item on a styrene project and may represent 5 to 10% of the entire plant cost. The maximum capacity of a styrene facility has in the past been limited by the technology available for construction of an EB Recycle Column.

A need thus exists for new technology which will avoid most, if not all, of the problems, limitations, and high costs normally involved in the construction, operation, and maintenance of large scale distillation facilities for separation and purification of vinylaromatic monomers, such as styrene. This invention is deemed to fulfill this need in an efficient and effective manner.

SUMMARY OF THE INVENTION

This invention comprises a substantial number of embodiments providing improvements in the design, construction, and operation of vinylaromatic distillation facilities, especially facilities for the recovery and purification of styrene monomer. Thus this invention has a number of objectives ("objects") not all of which necessarily apply to each embodiment of the invention. Subject to this caveat, the following are among the objects of this invention:

to provide a new and improved process for the distillation of readily polymerizable vinylaromatic monomers, especially styrene monomer;

to provide a new and improved process for the distillation of readily polymerizable vinylaromatic monomers, especially styrene monomer, which process results in higher recovery of high purity monomer and concomitantly in the production of less undesirable by-products;

to provide a new and improved process for the distillation of vinylaromatic monomers, especially styrene monomer, which results in the production of substantially less polymerized material in the distillation apparatus;

to provide a new and improved process for the distillation of vinylaromatic monomers, especially styrene monomer, which permits the distillation apparatus to be operated at an increased rate of throughput with improved efficiency;

to provide a new and improved process for the distillation of vinylaromatic monomers, especially styrene monomer, wherein the distillation efficiency is improved to the extent that overall product is improved;

to provide a process for the distillation of styrene monomer wherein the efficiency of the distillation is improved thereby reducing the recycle of styrene monomer to the styrene reactors with the resultant improvement in yield and catalyst life;

to drastically reduce the size of the distillation equipment required for a given production rate, thereby significantly reducing the capital cost of a new styrene monomer production facility or significantly reducing the capital cost of debottle necking an existing styrene monomer production facility;

to provide the capability of recycling ethylbenzene in the vapor state to the styrene reactors thereby reducing the overall energy demand;

to enable replacement or modification of one or more columns in an existing vinylaromatic distillation facility to improve the operation of that facility;

to make possible the installation of new vinylaromatic distillation facilities having very large capacity and throughput, yet requiring only three distillation columns.

In accordance with this invention it is now possible to substantially improve processes involving distillation of streams that contain vinylaromatic monomer, and especially streams that contain styrene monomer. For example, it is now possible to provide, pursuant to this invention, new distillation plant facilities for styrene production plants in which the distillations only require three distillation towers to produce high purity styrene monomer. Moreover these towers can be substantially smaller and less expensive than new distillation facilities of conventional size and design for such use. This invention also makes possible substantial improvements in existing facilities for recovering styrene or like vinylaromatic monomers from their corresponding production process streams. One option made available by this invention is to modify the configuration and/or mode of operation of one or more existing columns of the existing facility without total replacement of any existing column. Another option made possible by this invention is replacement of one or more existing columns with columns configured and operated in accordance with this invention. The choice among the various approaches made possible by this invention will thus depend upon the particular needs and circumstances existing at any given plant site.

In accordance with one aspect of this invention, the distillation of styrene or other readily polymerizable vinylaromatic monomer is conducted in equipment designed and operated with extremely low residence time. Thus this invention provides in one embodiment a process for the separation of purified vinylaromatic monomer as distillation overhead from a liquid mixture comprising vinylaromatic monomer in combination with polymerization inhibitor, heavy aromatics (i.e., aromatic hydrocarbon components having boiling points higher than that of the vinylaromatic monomer), and/or vinylaromatic tar residue, which process comprises continuously feeding that mixture to a packed distillation column in which the average residence time of liquid, inhibitor-depleted vinylaromatic monomer distillate overhead inside that column is less than 60 seconds. In addition, preferably the average total residence time of all liquid materials within that column is less than 15 minutes, and most preferably is less than 10 minutes, especially when the monomer is styrene.

Another embodiment provides a process for the separation of purified vinylaromatic monomer from a liquid mixture comprising vinylaromatic monomer in combination with polymerization inhibitor, aromatic hydrocarbon components having boiling points higher than that of the vinylaromatic monomer, and/or vinylaromatic tar residue, which process comprises continuously feeding that mixture to a packed distillation column operating under conditions effecting such separation, and recovering purified vinylaromatic monomer as overhead from that column. In this embodiment (i) the total annual production capacity per square foot of cross section of that column is in the range of about 9000 metric tons to about 22,000 metric tons or (ii) the column is operated at a reflux ratio in the range of about 1.1 to about 5 times the minimum reflux ratio for said column. Most preferably both of the conditions of (i) and (ii) are used in this embodiment.

In another aspect of this invention, the operating pressure of the distillation train is elevated to the range of about 10 psia to about 20 psia. Operation in this pressure range allows several enhancements to the process which significantly reduces system residence time. For example, at pressures in this range, cross-sectional area requirement in the columns is much less than in columns of current design for use in styrene recovery and purification. Moreover, the smaller cross-sectional area in turn permits the use of structural packing in the third or finishing column of distillation trains of this invention. So far as is known, this is a feature which has not been possible in commercial styrene recovery and purification systems of conventional construction and configuration.

These and other objects, features, aspects, advantages and embodiments of this invention will become still further apparent from the ensuing description, appended claims and accompanying drawings. To this end, the individual subject matter of each of the original claims appended hereto is incorporated into this portion of the specification as if fully set forth herein.

BRIEF DESCRIPTION OF THE DRAWINGS

FIG. 1 is a schematic representation of a typical commercial styrene recovery and purification installation used in accordance with the prior art.

FIG. 2 is a schematic depiction of another typical commercial installation for the recovery and purification of styrene monomer utilizing prior art principles.

FIG. 3 is a schematic representation of one type of three-column distillation train for use in accordance with this invention for the recovery and purification of styrene or other similar readily polymerizable vinylaromatic monomer.

FIG. 4 is a schematic depiction of another type of three-column distillation arrangement for use in the practice of this invention.

FIG. 5 is a top view in section taken along line 5,5 of FIG. 4 illustrating a preferred configuration for the bottom portion of a distillation tower employed in accordance with this invention.

FIG. 6 is a side view in section illustrating a preferred configuration of the bottom portion of a distillation tower used pursuant to this invention.

FIG. 7 is a side view in section illustrating an optional tower bottom system that may be employed with the distillation towers employed in the practice of this invention, normally the EB and/or BT towers.

FIG. 8 is a top view of a liquid distributor of a preferred configuration for use in the packed distillation columns of a styrene distillation facility provided pursuant to this invention.

FIG. 10 is a graphical representation of the polymerization rate of styrene containing a typical inhibitor, as a function of temperature.

FIG. 11 depicts in graph form the Gilliland correlation between the number of theoretical stages and reflux ratio.

FIG. 12 is a plot of structural packing performance expressed as the height equivalent to a theoretical plate versus vapor rate.

In FIGS. 3–9B like numerals are used to represent like parts in the systems or items depicted.

FURTHER DESCRIPTION OF THE INVENTION

Figure 9A:
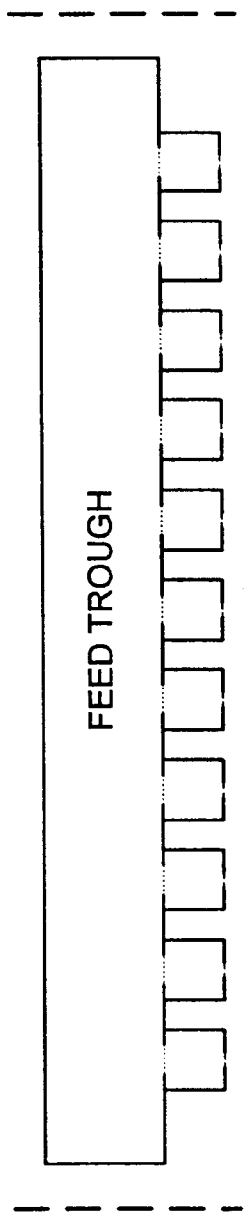
FIGS. 9A and 9B are side views in section of a liquid distributor of FIG. 8

As indicated in FIGS. 1 and 2 current conventional commercial practice involves recovering and purifying styrene by use of a system requiring four distillation columns or towers. These are generally referred to in the art as (1) a BT Column where benzene and toluene are separated and recovered from the process effluent from the styrene production facilities, (2) an EB Recycle Column in which ethylbenzene is recovered for recycle to the production facilities, and (3) a Finishing Column and (4) a Recovery Column in which the styrene is recovered and purified. As noted above, and as depicted in FIGS. 1 and 2, the Finishing Column and Recovery Column are both trayed columns, and both are needed to provide the number of trays required to process and purify the large volumes of product materials formed in modern large scale styrene production facilities.

In sharp contrast, and as illustrated in FIGS. 3 and 4, a complete distillation facility for processing styrene or like highly-polymerizable vinylaromatic monomer in the manner of the present invention requires only three distillation columns if suitably designed, constructed and operated as herein described.

Referring specifically to FIG. 3, the feed from the styrene production facilities (not shown) is transferred by line 10 into heat exchanger 12 and thence into an intermediate portion of column 14, the first of a train of three distillation columns or towers 14, 44, 74 connected in series. Inhibitor is introduced into the feed via line 16 so that the inhibitor is present in the feed as it is heated in heat exchanger 12. In the preferred system depicted, columns 14, 44, and 74 are all packed columns, each containing at least two beds of structured packing 15. The overhead in column 14 is passed by line 18 into condenser or cooler 20 and thence into reservoir 22. A portion of the condensed overhead is returned to the upper portion of tower 14 by line 24. Recovered benzene-toluene is discharged from reservoir 22 via line 26.

As indicated in FIG. 3 in the preferred form depicted, the bottom portions of towers or columns 14, 44, and 74 are configured in the same general manner as described in detail hereinafter in connection with FIGS. 5 and 6.

Typically the bottoms from column 14 in a system of FIG. 3 will comprise styrene monomer, ethylbenzene, inhibitor, and aromatic hydrocarbon components having boiling points higher than that of styrene. Tarry residues may also be present. The bottoms from column 14 are transferred by line 28 into an intermediate portion of column 44 which is operated under conditions to separate ethylbenzene as overhead and styrene, inhibitor, aromatic hydrocarbon components having boiling points higher than that of styrene, and if present, styrene tar residues, as bottoms from column 44. To control or inhibit tar formation, fresh inhibitor is introduced into tower 44 by line 40 at a location above the feed from line 28. The overhead from column 44 is carried via line 48 into condenser or cooler 50 and thence into reservoir 52. A portion of the overhead is returned to the upper portion of column 44 by line 54. Line 56 transfers the recovered ethylbenzene back to the styrene production facilities. The bottoms from column 44 are transmitted by line 58 to an intermediate portion of column 74. Column 74 is operated under conditions to enrich the overhead in purified styrene so that purified styrene may be recovered as overhead and so that the higher boiling residues can be removed as bottoms from column 74. Thus overhead from column 74 is transmitted by line 78 into condenser or cooler 80 and thence into reservoir 82. A portion of the overhead in reservoir 82 is returned to the top portion of column 74 via line 84. Purified styrene product is discharged from reservoir 82 via line 86.

In a preferred, but optional, aspect of the system of FIG. 3, a vacuum (i.e., a reduced pressure) is imposed on the material in condenser or cooler 80 by vacuum system 90 so that volatiles (e.g., ethylbenzene) remaining in the purified styrene can be purged therefrom and recycled via lines 94 and 98, for example, ultimately to line 56 via the overhead subassembly of column 44 such as through condenser or cooler 50, as illustrated. Line 98 can, of course, be connected to carry the volatiles directly to reservoir 52 or to line 56, if desired.

The system depicted in FIG. 4 is essentially the same as that of FIG. 3 except that the feed from the styrene production facilities is first processed in column 44, and the overhead therefrom is processed in column 14 whereas the bottoms from column 44 are processed in column 74. Thus in effect the largest column 44 is used to separate all materials boiling below styrene as overhead and, as in the system of FIG. 3, separation and purification of the styrene monomer is effected in column 74, the finishing column. The overhead from column 44 is transferred from column 44 to and processed in column 14 to recover the benzene-toluene fractions as overhead and ethylbenzene as the bottoms from column 14. Thus the production feed plant enters the distillation train of FIG. 4 via line 30 to column 44, and the overhead discharged from column 44 via line 56 is fed into column 14 via line 10.

Accordingly, in the system of FIG. 4 the overhead from column 44 comprises low boiling aromatic hydrocarbons (principally benzene and toluene) and ethylbenzene. The bottoms from column 44 in FIG. 4 comprise mainly styrene monomer, inhibitor, and aromatic hydrocarbons having boiling points higher than that of styrene. Tar may also be present. The overhead from column 14 in FIG. 4 comprises benzene and toluene, and the bottoms from column 14 in FIG. 4 comprises mainly ethylbenzene which typically is recycled to the styrene production reactor of the styrene production plant facilities.

FIGS. 5 and 6 illustrate in larger view the preferred configuration of equipment for the bottom portions of columns 14, 44 and 74 of FIGS. 3 and 4. Referring to FIGS. 5 and 6, trap out tray 32 traverses a substantial cross-sectional area of the column, and has a plurality of apertures 35 therein. The upper side of tray 32 has individual upstanding vapor chimneys 36 surrounding each individual aperture. Chimneys 36 are in effect short lengths of upstanding pipe that keep apertures 35 free of downcoming liquid in the column so that the liquid collecting on the top side of tray 32 is directed to the open zone 34 and thence into an internal baffled section composed of catch basin or trough 60 and baffle plates 62 and 64. Trough 60 and baffle plates 62 and 64 extend arcuately around the internal perimeter of the column below open zone 34 so as to isolate or segregate the liquid passing into zone 34 and thence into trough 60 from all other liquid in the lower part of the column. Baffle plates 62 and 64 and trough 60 are spaced apart so that passage of vapors between them is not blocked. Liquid collected in trough 60 is transferred via line 55 as inlet to reboiler 65 which converts the liquid into a liquid phase and a vapor phase which are transmitted from reboiler 65 into the column in the space below tray 32 by conduit 66. The vapor phase thus passes upwardly through apertures 35 and chimneys 36 and thence up the column. The lowermost portion of the column has a reduced diameter portion 68, and the liquid phase from conduit 66 flows or drops downwardly into reduced diameter portion 68. It will be seen that baffle plates 62 and 64 prevent any of this liquid phase from entering trough 60. Therefore the bottom portions of the columns are equipped with one-pass reboiler systems. Temperature control in reboiler 65 is accomplished by the feed of steam into the reboiler via line 70. Condensed water is removed from reboiler 65 by line 72.

FIG. 7 illustrates an optional modification of the apparatus of FIGS. 5 and 6 which is used usually in connection with columns 14 and 44 if additional surge is required. In such case the reduced diameter portion 68 of these columns is in the form of a conduit or pipe which transmits the liquid phase (released from conduit 66) from the bottom of the column and through cooler or condenser 88 into surge pot 92. Pump 96 provides the additional surge for transmitting to the next column this liquid phase emanating from reboiler 65 and collected in surge pot 92. Ordinarily the system of FIG. 7 is not required for column 74, but may be installed thereon if desired.

It will be appreciated that FIGS. 3 through 9B are schematic in character. Thus FIGS. 3 through 9 exclude various pumps, control valves, motors, filters, and other auxiliaries or elements that are typically used in the design and operation of distillation columns.

In FIGS. 6 and 7 liquid in reduced diameter portion 68 and in surge pot 92, respectively, is pumped forward by means of level control 99 which suitably controls the operation of the pumps by means of a control valve (not shown) on the pump discharge line.

Reboiler 65 should be close coupled to its tower to minimize piping. It is also possible to enclose the reboiler in the bottom portion of its tower.

Figure 9B:
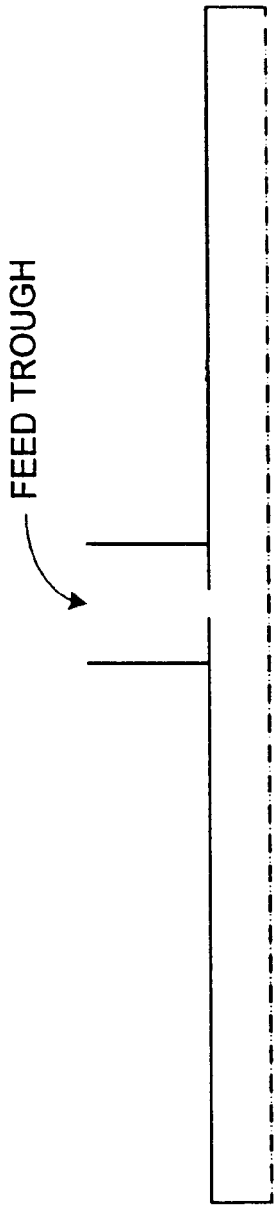

FIGS. 8–9B illustrate the liquid distributors 25 which are disposed horizontally between beds of packing 15 in each packed column of the system. The distributor is composed of a primary trough or pipe 25 which distributes the liquid into a series of secondary troughs or pipes 45 beneath and perpendicular to the primary trough or pipe. This secondary series of troughs or pipes is equipped with a series of drip points or holes 75 to thereby distribute the liquid uniformly over the top of the packing 15.

When employing one of the preferred three-column systems such as illustrated in FIGS. 3 and 4, the pressures in the three columns 14, 44 and 74 are maintained within the range of about 10 to about 20 psia. When using such system to process styrene monomer product from a styrene production facility, the relationship between distillation pressure and temperature in these columns operated at a nominal pressure of 15 psia is shown in Table 2. For comparative purposes the same information for a conventional styrene distillation facility of the prior art (already presented in Table 1) is repeated in Table 2.

TABLE 2

Styrene Distillation Pressure and Temperature Relationships

| Distillation Column | Column Portion | Prior Art | | The Invention | |
|---|---|---|---|---|---|
| | | Pressure, psia | Temperature, Degrees F. | Pressure, psia | Temperature, Degrees F. |
| BT Column | Top | 4.0000 | 145 | 15.0000 | 221 |
| | Bottom | 4.5029 | 207 | 15.2500 | 288 |

TABLE 2-continued

Styrene Distillation Pressure and Temperature Relationships

| Distillation Column | Column Portion | Prior Art | | The Invention | |
|---|---|---|---|---|---|
| | | Pressure, psia | Temperature, Degrees F. | Pressure, psia | Temperature, Degrees F. |
| EB Recycle | Top | 1.4500 | 162 | 15.0000 | 275 |
| | Bottom | 2.9780 | 206 | 15.9000 | 299 |
| Styrene Finishing | Top | 1.1000 | 159 | 15.0000 | 293 |
| | Bottom | 1.2159 | 192 | 15.6000 | 298 |
| Styrene Recovery | Top | 2.5145 | 159 | N/A | N/A |
| | Bottom | 3.9458 | 289 | N/A | N/A |

Besides pressure and temperature control, a number of other factors are of importance in achieving all of the advantages made possible by this invention. As pointed out above, one very important factor is the average residence or retention time of the liquid distillate overhead in the respective columns. Also of importance is the average total residence time of all liquids within the respective columns. In general the columns in the distillation processes of this invention are designed, constructed and operated such that these residence or retention times are much smaller in duration than the times utilized in conventional commercial practice in accordance with the prior art. By way of illustration, a standard commercial styrene distillation facility with a capacity of 200,000 metric tons per year will typically have a total liquid retention time in the conventional 4-column train of over 6 hours. In contrast, it is possible pursuant to this invention to provide a 3-column styrene distillation facility of the same capacity having a total liquid retention time substantially less than 1 hour, e.g., as low as about 35 minutes.

In addition to increased pressure and temperature, factors contributing to this vast improvement include reduced column size; use of structural packing in all three columns; use of tower bottom modifications of the type described above in connection with FIGS. 5 and 6 and/or 7; use of liquid distributors of the type described above in connection with FIGS. 8–9B use of suitable feed rates to the columns; and other factors discussed below.

Operating Pressures

The current styrene distillation train such as depicted in FIGS. 1 and 2 uses inhibitor and low temperature produced by low pressure operation to minimize polymer production. The overall process of this invention (FIGS. 3 and 4) also use inhibitor; however, the primary control of polymerization is residence time. In the process of this invention temperatures are in general maintained as low as possible consistent with the other new operating conditions. Also, the column pressures are usually increased to slightly above atmosphere pressure, although in certain cases vacuum may be used to maximize efficiency and to provide more capacity flexibility. Thus except in special cases, the new overall systems of this invention (e.g., FIGS. 3 and 4) operate in the range of 10 psia to 20 psia compared to 1 to 4 psia for existing plants. Intermediate pressures may be used in applying portions of the technology of this invention to existing plants.

Total Liquid Volume and Liquid Retention Times

Polymerization rate is defined as percent polymerized each hour the styrene is maintained at a given temperature. Other factors such as composition (the lower the concentration the lower the polymerization rate at a given temperature) may affect the rate slightly; however, with a given inhibitor, polymerization is primarily a function of time and temperature. Since temperature has the most significant effect on rate, prior art efforts have concentrated on temperature reduction. Time is a linear function with total polymerization (i.e., if time is doubled, total polymer will approximately double at a set temperature).

Table 3 exhibits the residence time in a typical styrene distillation train. While these calculations are based on a 200,000 metric ton per year styrene plant operated at a pressure of 15 psia, other sized plants will in general have similar relative residence times. The second half of Table 3 shows the same residence calculations for a new distillation train of this invention having a capacity of 200,000 metric tons per year. Residence times are about 8% of the current technology. Therefore, polymerization rates of over 12 times as high may be allowed to occur without increasing the level of polymer over that normally formed.

purposes, to adjust the dimensions of Table 3 for a facility of a different capacity, those dimensions can be multiplied by the expression $$\frac{C}{200,000}$$

where C is the capacity of the facility in metric tons per year. To adjust the dimensions in Table 3 for use of pressures different from 15 psia, the dimensions should be multiplied by the expression $$\frac{15}{P}$$

TABLE 3

Liquid Volume/Retention Time Calculations

| | Prior Art | | | | Design of the Invention | | |
|---|---|---|---|---|---|---|---|
| | T-1 | T-2 | T-3 | T-4 | T-1P | T-2P | T-3P |
| Upper Size | | | | | | | |
| Diameter - (Ft.) | 5.00 | 16.50 | 11.60 | 7.00 | 3.50 | 8.00 | 4.00 |
| Area - (Sq. Ft.) | 19.63 | 213.82 | 105.68 | 38.48 | 9.62 | 50.27 | 12.57 |
| Lower Size | | | | | | | |
| Diameter - (Ft.) | 5.00 | 16.00 | 11.60 | 5.60 | 3.50 | 8.00 | 4.00 |
| Area - (Sq. Ft.) | 19.63 | 201.06 | 105.68 | 24.63 | 9.62 | 50.27 | 12.57 |
| Feed | | | | | | | |
| Percent Styrene | 60.0% | 62.5% | 60.0% | 98.0% | 60.0% | 62.5% | 98.0% |
| Rate - (GPM) | 166.7 | 160 | 100 | 20 | 166.7 | 160 | 100 |
| Volume Distribution | | | | | | | |
| Quantity | 1 | 4 | 24 | 33 | 1 | 4 | 3 |
| Thickness - (In.) | 8 | 8 | 3 | 3 | 4 | 4 | 4 |
| Thickness - (Ft.) | 0.667 | 0.667 | 0.250 | 0.250 | 0.333 | 0.333 | 0.333 |
| Volume (Cu. Ft.) - (Thickness * Area) | 13.09 | 544.67 | 634.10 | 272.47 | 3.21 | 67.02 | 12.57 |
| Volume Packing | | | | | | | |
| Percent Hold Up | 4.00% | 4.00% | | | 4.00% | 4.00% | 4.00% |
| Height of Packing - (Ft.) - Upper Section | 20 | 50 | | | 25 | 60 | |
| Height of Packing - (Ft.) - Lower Section | 20 | 84 | | | 25 | 90 | 90 |
| Volume (Cu. Ft.) - (Height · Area * % Holdup) | 15.71 | 1103.22 | | | 9.62 | 301.59 | 45.24 |
| Bottom Head | | | | | | | |
| 2/3 * pi * 1/4 * R³ | 8.18 | 268.08 | 102.16 | 22.99 | 2.81 | 4.19 | 2.09 |
| Bottom Shell | | | | | | | |
| Height of Liquid - (Ft.) | 2 | 2 | 4 | 6 | 4 | 4 | 4 |
| Volume (Cu. Ft.) - (Height * Area) | 39.27 | 402.12 | 422.73 | 147.78 | 9.62 | 50.27 | 8.38 |
| Reboiler & Piping | | | | | | | |
| Estimated - (Cu. Ft.) | 10 | 50 | 20 | 20 | 10 | 50 | 30 |
| Total Cubit Feet | 86 | 2,368 | 1,179 | 463 | 35 | 473 | 98 |
| Conversion to gallons (7.48 * Cu. Ft.) | 645 | 17.713 | 8.819 | 3,465 | 264 | 3,539 | 735 |
| Minutes Retention Time | 3.87 | 110.71 | 88.19 | 173.25 | 1.58 | 22.12 | 7.35 |
| Total Minutes Retention Time = = = > 376.02 | | | | | | | 31.05 |
| Percent of Original = = > 8.3% | | | | | | | |

It will be seen from Table 3 that the total retention time can be greatly reduced by the practice of this invention!

It is to be noted that Table 3 sets forth particularly preferred dimensions for new or replacement packed cylindrical columns for a distillation facility having a capacity of 200,000 metric tons per year and operated at a pressure of 15 psia. A detailed computer simulation is required to size the equipment such as columns, trays, and the like, for other capacities and pressures. However for preliminary sizing where P is the operating pressure in the column in psia. Both such adjustments should be used in cases where the capacity differs from 200,000 metric tons per year and the pressure differs from 15 psia. It will be understood that suitable departures may be made from the actual or adjusted dimensions of Table 3 inasmuch as those dimensions represent particularly preferred embodiments of the invention. Those skilled in the art can readily modify such dimensions and conditions to satisfy any given set of circumstances, using the principles of this invention and the information pertaining thereto presented herein as the basis of such modifications.

Use of Only One Column to Distill Inhibitor-Free Monomer

Commercial styrene plants use a four tower distillation train (see FIGS. 1 and 2). Product styrene is taken overhead in both the Styrene Finishing Column and the Styrene Recovery Column. Both columns have a section where high purity styrene is distilled with no inhibitor. This is because conventional styrene inhibitors are non-volatile liquids and thus they do not go above the feed tray. The total liquid residence time for both of the prior art product towers in the uninhibited zone is typically at least 90 minutes. In sharp contrast, pursuant to this invention the liquid residence time in the uninhibited zone of the packed finishing column for liquid vinyl aromatic monomer is less than 60 seconds and for liquid inhibitor-free styrene is preferably less than 30 seconds. This means that the polymerization rate can be 180 times as high to limit the polymer formation to the same quantity. This in turn enables the temperature in the column to be greatly increased (e.g., from the current temperature of about 159° F. to as high as about 312° F.) without the amount of polymer formed in the liquid inhibitor-free monomer exceeding the amount formed in the third and fourth columns of a conventional system such as illustrated in FIGS. 1 and 2.

Cross Sectional Area of Columns

All three towers such as depicted in FIGS. 3 and 4 are operated at near atmospheric pressure. When the pressure is increased the temperature will also increase based on the boiling points of the chemical mixtures being distilled.

Column cross sectional area is based on the volume of vapor flow rate required. This volume will decrease as pressure increases and will increase as temperature increases. At the ranges of operation for styrene distillation, pressure has greater effect than temperature.

The relationship of pressure, temperature and volume is stated as:

$$\frac{P1V1}{T1} = \frac{P2V2}{T2}$$

where pressure is in psia, absolute temperature in degrees Rankin ("R") is (° F.+460), and volume is in ft$^3$. As an example: If the pressure of the EB Column is increased from 1.45 psia to 2.90 psia, the temperature will increase from 619° R. to 654° R. Therefore:

$$\frac{P1V1}{T1} = \frac{P2V2}{T2}$$

$$\frac{(1.45psia)V1}{619° R.} = \frac{(2.90psia)V2}{654° R.}$$

$$\frac{V1}{V2} = \frac{290psia(619° R.)}{1.45psia(654° R.)}$$

Thus if V1 is 1ft$^3$, then V2 is 0.53ft$^3$.

As demonstrated, by increasing the pressure slightly, the cross sectional area requirements have been reduced to 53% of the original. Actual column simulations demonstrate that the EB Recycle Column cross sectional area can be reduced to less than 20% of the original. Since diameter is no longer the primary concern, a reduction to 25% of the original cross sectional area was chosen for purposes of illustration.

Since Area=$\pi r^2$, if the area is to be 25% the diameter is cut in half. For the EB Recycle Column, if no other changes were made, the residence time would be cut by 75%.

Structural Packing

All three columns in a new facility of this invention are equipped with structured packing. Even when upgrading an existing distillation facility at least one of the columns, most preferably at least the finishing column, will be equipped with structured packing. As discussed in the previous section, the cross sectional area of each column can be reduced because higher pressures are preferably used in the three-column systems of this invention. Since the new liquid rates are close to the old rates, the liquid loading per square foot of area will increase, and therefore with sufficient liquid loading, all three columns such as depicted in FIGS. 3 and 4 use structured packing.

Packed towers have lower liquid hold up than trayed columns with the same number of equivalent stages. A trayed tower with a cross sectional area of 10 ft$^2$ and a tray efficiency of 80% has a liquid hold up at about 3.125 ft$^3$ per theoretical stage. A structured packing tower with an area of 10 ft$^2$ and a height equivalent to a theoretical plate (HETP) of 18 inches will have a liquid hold up of only 0.60 ft$^3$. Assuming the same height of packing, the reduction in area greatly reduces the volume of packing required in BT Column and the EB Recycle Column which typically are packed in the old designs of the prior art. The liquid hold up for a styrene distillation tower of this invention is typically about 4% of the packing volume. The total liquid holdup will decrease proportionally to the area decrease.

Distributor Configuration

In accordance with this invention, the liquid distributors above each bed of packing are smaller because the diameters of the columns are smaller compared to conventional styrene distillation columns of the same capacity. Smaller tower diameters and larger liquid loading per square foot make the tower less susceptible to maldistribution. This fact makes it possible to further reduce the liquid holdup in the distributor. Thus a slightly lower efficiency distributor with a 4-inch liquid depth is preferably used instead of the standard 8-inch liquid depth distributor.

Tower Bottom Modifications

The type of modifications which are preferably used pursuant to this invention have been described above in connection with FIGS. 5, 6 and 7. In essence, these modifications involve three basic aspects, (1) use of a trap out tray feeding to a one-pass reboiler, (2) use of minimized heights in the bottom portion of the tower, and (3) maintaining minimum product inventory in a head of reduced volume as compared to a conventional tower used for the same distillation. Suffice it to say here that these modifications minimize residence time in the tower, and this is of particular advantage inasmuch as the tower bottoms are the hottest part of any distillation column.

Integral Condenser and Reboiler

The use of an integral condenser and/or reboiler provides further reduction in residence time. Installation of the exchangers inside the columns both removes column volume and reduces piping volume. This enhancement is an optional, but preferred additional feature of this invention.

Inhibitor Injection

Many different inhibitor injection points have been used in commercial plants. Normally inhibitor is injected into the feed of the first tower and carried through the tower system with the heavies. A slip stream of the final residue is usually recycled to maintain inhibitor level. In the practice of this invention the same system may be used depending on the characteristics of the inhibitor employed. Another method is to inject inhibitor into the liquid distributor above the second bed of each tower. Heavies recycle should be stopped wherever possible.

A number of inhibitors are available for use in the process. Among materials used to inhibit undesirable polymerization of styrene or other readily polymerizable vinyl aromatic monomers during distillation are 2,6-dinitro-p-cresol, dinitro-o-cresol, tert-butylcatechol, styrene tar, sulfur, and combinations such as 2,6-dinitro-p-cresol and a phenylene diamine, 2,6-dinitro-p-cresol and 4-tert-butylcatechol, phenothiazine and tert-butylcatechol, and others. As is known in the art, a number of such polymerization inhibitors should be utilized in conjunction with oxygen or air to enhance performance. Recently, improved inhibitors of unspecified composition have appeared in the market place.

Efficiency

Distillation tower efficiency may be defined in several ways. In the case of new tower construction, efficiency can be considered to be the relative number of theoretical stages required to make the required separation. In packed towers the theoretical stages may be converted to height of packing required.

Relative volatility is a measurement of difficulty of separation. When the temperatures in the EB Recycle Column are increased, the relative volatility decreases indicating a more difficult separation. Computer simulation of an EB Recycle Column shows that approximately 100 stages are needed at atmospheric conditions to make the same separation as 92 stages at low pressure (1.5 psia). Therefore, a small loss of efficiency occurs in the EB Recycle Column when operated at higher pressures. Other columns are not affected in this manner. Several other factors increase the efficiency, and more than compensate for the small loss of efficiency in the EB Column. The improvements to efficiency are:

1. Replacement of trays
2. Better Distillation
   a. Decreased diameter
   b. Higher liquid loading
   c. Decreased velocity
3. Reboiler configuration
4. Flexible Reflux Ratio
5. Optimal Loading
6. EB Recycle A brief discussion of each of these improvements follows:

1. Replacement of Trays

For low to moderate pressure distillation columns, packed columns are smaller and less expensive for the same separation. One of the major advantages of a three-column system of this invention is the use of packing in the finishing tower, so that a fourth tower is no longer needed for producing highly pure monomer.

2. Better Distribution

As the area is reduced for example to 25% of the original, the liquid loading per ft$^2$ (with no other changes) is multiplied by four. Also, as styrene is heated, the viscosity drops allowing a faster and a smoother liquid flow. These three factors improve the efficiency so that the 100 stages will require less height of packing than the original 92 stages.

3. Reboiler Configuration

The baffled tower better separates all liquid which has gone through the reboiler from the liquid which has not. A reboiler by definition is one ideal stage. If the liquid from the outlet mixes with the liquid entering the reboiler some efficiency is lost. Standard practice is to consider a reboiler with mixing as one-half stage. By preventing the mixing, one-half stage is added to the tower.

4. Flexible Reflux Ratio

The number of stages required to make a given separation is a function of the reflux ratio. Since the design of towers in the systems of this invention is no longer constrained by liquid loading or tower diameters, the reflux ratio may be adjusted to a considerable extent. The designer thus now has the opportunity of optimizing the capital cost of the distillation facility by (i) increasing the reflux ratio, (ii) lowering the number of stages required, and (iii) reducing the height of packing.

This ability to adjust reflux ratio may also be used to improve product quality or to purify the recycle streams thereby improving product yield.

5. Optimal Loading

As can be seen from FIG. 12, the efficiency of structural packing is constant for most of the range of vapor loading. When vapor loading reaches approximately 90% of maximum loading, the vapor creates a turbulence in the liquid film resulting in high efficiency. As the flow increases, containment of liquid in the vapor begins and eventually flooding occurs.

This optimum point may be measured by the differential pressure from the top to bottom of the tower. If the tower is operated at this differential pressure, maximum efficiency will be achieved.

When a tower changes rates, this differential may be maintained by adjusting reflux rates. This adjustment is not always desirable and is usually not energy efficient.

Another way to adjust the differential pressure is to adjust the tower's overhead pressure as previously discussed. Continuous operation at maximum efficiency will minimize capital costs, and minimized energy consumption may be achieved by adjusting the pressure with vacuum jets. A small amount of motive steam to a vacuum jet can improve efficiency considerably. The EB Column and Styrene Finishing Column may be operated under a slight vacuum (in the range of about 10 psia to just below atmospheric pressure) to maximize efficiency in cases where this approach is selected. This method of enhancement is optional.

6. EB Recycle

The overhead product of the EB Recycle Column of FIG. 1 is recycled to the Styrene Reactors. Before the ethylbenzene enters the reactors it must be vaporized. An energy savings may be realized if the ethylbenzene in line 56 of FIG. 3 is recycled as a vapor from the overhead of the EB Recycle Column. This method of efficiency enhancement is also optional.

It is to be clearly understood and appreciated that the extensive number of improved features of this invention described above need not all be utilized in any given distillation facility for separation and recovery of purified monomer. The selection of the particular features in any particular situation will be governed by a number of considerations such as plant capacity, the vinylaromatic monomer being processed, the purity of the monomer desired or required, and of course, the overall economics and capital requirements of the operation. Generally speaking, however, the greater the number of such improved features used, the larger the improvement in the overall operation.

The application of the technology of this invention discussed above has been focused primarily on new plant construction. However, the same principles may be applied to existing plants to the extent required by the market and the capabilities of the rest of the plant. The range of application varies from replacement of the entire distillation train to educated adjustments in operating conditions pursuant to this invention. Following is a list of typical applications to existing plants:

A. Distillation Train Replacement

An older plant with no packed towers may find it more economical to replace the entire train. For example, the current cost to repack a 16-foot diameter EB Recycle column is about 3.1 million dollars. The cost to replace the entire column with an 8-foot diameter column is about 1.45 million dollars.

B. Replace a Single Column

If only one tower is the bottleneck in an existing facility, then it may be sufficient to simply replace that one tower with a tower embodying features of this invention.

C. Repack the Monomer Finishing Column

The new technology of this invention allows the use of packing in the monomer finishing column resulting in significant quality improvements and yield savings.

D. Modify Existing Columns

The column modifications described above, such as described with reference to one or more of FIGS. 5–9B inclusive, can be added to existing columns to achieve reduced residence times in those columns.

E. Differential Pressure Control

Change operating conditions as follows:
a) Set feed rate,
b) Ratio reflux to feed rate,
c) Set product overhead rates,
d) Adjust pressure to achieve the optimum differential pressure.

When applied to existing columns the increase in capacity is roughly equal to the increase in pressure. For example, a 10% capacity increase requires about a 10% pressure increase. Therefore existing columns may continue to be operated at relatively low pressure and still achieve marginal increases in capacity.

F. Conversion of Four Column to Three Column System

The Finishing Column (FC) and Recovery Column (RC) of an existing system may act as one column with minor modifications. The Finishing Column feed would be introduced through the FC Reboiler. The FC bottoms would be the RC reflux and the RC overhead vapor would go directly to the FC bottoms. An inhibitor injection point would be required near the old FC feed point. This system is less efficient than replacing the FC and RC with a finishing column of this invention. However, the conversion could be made quickly with less expense.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

I claim:

1. A process for the separation of purified vinylaromatic monomer as distillation overhead from a liquid mixture comprising vinylaromatic monomer, polymerization inhibitor, aromatic hydrocarbon components having boiling points above that of the vinylaromatic monomer, which process comprises continuously feeding said mixture to a packed distillation column in which the average residence time of liquid, inhibitor-depleted vinylaromatic monomer distillate overhead inside said column is less than 60 seconds.

2. A process according to claim 1 wherein said mixture is fed to an intermediate portion of said column.

3. A process according to claim 1 wherein the average total residence time of all liquid materials within said column is less than 15 minutes.

4. A process according to claim 1 wherein said monomer is styrene.

5. A process according to claim 4 wherein the average total residence time of all liquid materials within said column is less than 10 minutes.

6. A process according to claim 4 wherein the average residence time of liquid, inhibitor-depleted styrene monomer in said column of less than 30 seconds and the average total residence time of all liquid materials within said column is less than 10 minutes.

7. A process according to claim 6 wherein said column is operated at a pressure in the range of about 10 psia to about 20 psia.

8. A process according to claim 6 wherein a liquid distributor is disposed horizontally between beds of structured packing in said packed column, and is configured such that the liquid depth in said distributor is no more than about 4 inches.

9. A process according to claim 6 wherein the bottom interior portion of the column has a reduced diameter relative to the diameter of the column above said bottom interior portion; wherein all downcoming liquid below the bottom of the packing in the column is collected, segregated and converted into a liquid phase and a vapor phase; wherein the vapor phase is passed upwardly through the column for discharge as overhead; and wherein the liquid phase is passed downwardly into said bottom interior portion for discharge from said column.

10. A process according to claim 6 wherein said column is operated at a vapor loading in the range of about 90 to about 95% of maximum loading such that turbulence in the liquid film is maintained without the occurrence of flooding.

11. A process according to claim 4 wherein said mixture is fed at an intermediate portion of said column.

12. A process according to claim 11 wherein said column is operated at a pressure in the range of about 10 psia to about 20 psia.

13. A process according to claim 12 wherein a liquid distributor is disposed horizontally between beds of structured packing in said packed column, and is configured such that the liquid depth in said distributor is no more than about 4 inches.

14. A process according to claim 12 wherein the bottom interior portion of the column has a reduced diameter relative to the diameter of the column above said bottom interior portion; wherein all downcoming liquid below the bottom of the packing in the column is collected, segregated and converted into a liquid phase and a vapor phase; wherein the vapor phase is passed upwardly through the column for discharge as overhead; and wherein the liquid phase is passed downwardly into said bottom interior portion for discharge from said column.

15. A process according to claim 12 wherein the bottom portion of said column is equipped with at least (i) an internal trap out tray having a plurality of apertures therein, the upper side of the tray having individual vapor chimneys surrounding said apertures, (ii) an internal baffled section, (iii) a reboiler, (iv) a liquid transfer line from said baffled section to said reboiler, (v) a reboiler outlet line, and (vi) a reduced diameter bottom portion, such that:

A) the trap out tray collects all downcoming liquid below the bottom of the packing in said column and transfers the collected liquid to the baffled section;

B) the baffled section segregates said transferred liquid in a zone lower than said trap out tray;

C) the outlet line carries the segregated liquid to the reboiler;

D) the reboiler partially vaporizes the segregated liquid to produce a vapor phase and a liquid phase; and E) the reboiler outlet line transmits said vapor phase and said liquid phase to a discharge location in the column below the trap out tray so that said vapor phase passes upwardly through the apertures and vapor chimneys, and thence up the column, and said liquid phase passes downwardly into the reduced diameter bottom portion for discharge from said column.

16. A process for the recovery of purified vinylaromatic monomer which comprises:

a) continuously feeding a mixture comprising vinylaromatic monomer, ethylaromatic hydrocarbon, polymerization inhibitor, and aromatic hydrocarbon components having boiling points higher than that of the vinylaromatic monomer, to a packed separation column operated at a pressure in the range of about 10 psia to about 20 psia to separate ethylaromatic hydrocarbon as an overhead fraction and provide liquid bottoms comprising vinylaromatic monomer, polymerization inhibitor, and aromatic hydrocarbon components having boiling points higher than that of the vinylaromatic monomer;

b) continuously feeding liquid bottoms from said separation column into a packed finishing column that maintains an average residence time of liquid, inhibitor-depleted vinylaromatic monomer in said finishing column of less than 60 seconds; and c) continuously recovering purified vinylaromatic monomer as overhead from said finishing column.

17. A process according to claim 16 wherein said monomer is styrene and said ethylaromatic hydrocarbon is ethylbenzene; and wherein said finishing column maintains an average residence time of liquid, inhibitor-depleted styrene monomer in said finishing column of less than 30 seconds and an average total residence time of feed materials within said finishing column of less than 10 minutes.

18. A process according to claim 17 wherein said mixture is fed at an intermediate portion of said separation column; wherein additional inhibitor is introduced into said separation column above said intermediate portion of said separation column; and wherein said liquid bottoms are fed at an intermediate portion of said finishing column.

19. A process according to claim 16 wherein at least one of said separation column and said finishing column is operated at a pressure in the range of about 10 psia to about 20 psia.

20. A process according to claim 16 wherein both said separation column and said finishing column are operated, independently, at the same or different respective pressures in the range of about 10 psia to about 20 psia.

21. A process according to claim 17 wherein the bottom interior portion of said separation column or of said finishing column has a reduced diameter relative to the diameter of that one particular column above its bottom interior portion; wherein all downcoming liquid below the bottom of the packing in that one particular column is collected, segregated and converted into a liquid phase and a vapor phase; wherein the vapor phase is passed upwardly through that particular column for discharge as overhead; and wherein the liquid phase is passed downwardly into said bottom interior portion of that particular column for discharge from that particular column.

22. A process according to claim 17 wherein the bottom interior portion of said separation column and the bottom interior portion of said finishing column both have reduced diameters relative to their respective diameters above their respective bottom interior portions; wherein all downcoming liquid below the bottom of the packing in each respective column is individually collected, segregated and converted into a liquid phase and a vapor phase; wherein the respective vapor phases are passed upwardly through their respective columns for discharge as overhead; and wherein the respective liquid phases are passed downwardly into the respective bottom interior portions of their respective columns for discharge from their respective columns.

23. A process according to claim 17 wherein the bottom portion of said separation column and the bottom portion of said finishing column both are equipped, individually, with at least (i) an internal trap out tray having a plurality of apertures therein, the upper side of the tray having individual vapor chimneys surrounding said apertures, (ii) an internal baffled section, (iii) a reboiler, (iv) a liquid transfer line from said baffled section to said reboiler, (v) a reboiler outlet line, and (vi) a reduced diameter bottom portion, such that:

A) the trap out tray collects all downcoming liquid below the bottom of the packing in that column and transfers the collected liquid to the baffled section;

B) the baffled section segregates said transferred liquid in a zone lower than said trap out tray;

C) the outlet line carries the segregated liquid to the reboiler;

D) the reboiler partially vaporizes the segregated liquid to produce a vapor phase and a liquid phase; and E) the reboiler outlet line transmits said vapor phase and said liquid phase to a discharge location in that column below the trap out tray so that said vapor phase passes upwardly through the apertures and vapor chimneys, and thence up the column, and said liquid phase passes downwardly into the reduced diameter bottom portion for discharge from that column.

24. A process according to claim 23 wherein a liquid distributor is disposed horizontally between superposed beds of structured packing in said separation column or in said finishing column or in both of said columns, and wherein each liquid distributor is configured such that the liquid depth therein is no more than about 4 inches.

25. A process according to claim 17 wherein either said separation column or said finishing column is operated at a vapor loading in the range of about 90 to about 95% of maximum loading such that turbulence in the liquid film in said column is maintained without the occurrence of flooding.

26. A process according to claim 17 wherein said separation column and said finishing column are both operated at vapor loadings in the range of about 90 to about 95% of maximum loading such that turbulence in the liquid film in said columns is maintained without the occurrence of flooding.

27. A process for the recovery of purified vinylaromatic monomer from a mixture comprising vinylaromatic monomer, ethylaromatic hydrocarbon, at least one aromatic hydrocarbon that has a lower boiling point than the ethylaromatic hydrocarbon, and at least one aromatic hydrocarbon that has a higher boiling point than those of the ethylaromatic hydrocarbon and the vinylaromatic monomer which process comprises:

a) continuously feeding said mixture and polymerization inhibitor to a first packed separation column to separate as an overhead fraction aromatic hydrocarbon that has a lower boiling point than the ethylaromatic hydrocarbon and provide first liquid bottoms comprising vinylaromatic monomer, polymerization inhibitor, ethylaromatic hydrocarbon and aromatic hydrocarbon that has a higher boiling point than those of the ethylaromatic hydrocarbon and vinylaromatic monomer;

b) continuously feeding first liquid bottoms to a second packed separation column to separate ethylaromatic hydrocarbon as an overhead fraction and provide second liquid bottoms comprising vinylaromatic monomer, polymerization inhibitor, and aromatic hydrocarbon having a higher boiling point than those of the ethylaromatic hydrocarbon and vinylaromatic monomer;

c) continuously feeding second liquid bottoms into a packed finishing column that maintains an average residence time of liquid, inhibitor-depleted vinylaromatic monomer in said finishing column of less than 60 seconds; and d) continuously recovering purified vinylaromatic monomer as overhead from said finishing column.

28. A process according to claim 27 wherein the mixture fed to said first separation column comprises styrene monomer, ethylbenzene and toluene; and wherein said column maintains an average residence time of liquid, inhibitor-depleted styrene monomer in said finishing column of less than 30 seconds and an average total residence time of feed materials within said finishing column of less than 10 minutes.

29. A process according to claim 28 wherein said mixture is fed at an intermediate portion of said first separation column; wherein first liquid bottoms are fed at an intermediate portion of said second separation column; wherein additional inhibitor is introduced into said second separation column above said intermediate portion of said second separation column; and wherein second liquid bottoms are fed at an intermediate portion of said finishing column.

30. A process according to claim 28 wherein at least one of said first separation column, said second separation column and said finishing column is operated at a pressure in the range of about 10 psia to about 20 psia.

31. A process according to claim 28 wherein at least two of said first separation column, said second separation column and said finishing column are operated at the same or different pressures in the range of about 10 psia to about 20 psia.

32. A process according to claim 28 wherein all three of said first separation column, said second separation column and said finishing column are operated at the same or different pressures in the range of about 10 psia to about 20 psia.

33. A process according to claim 28 wherein the bottom interior portion of at least one of said first separation column, said second separation column, and said finishing column has a reduced diameter relative to the diameter of said at least one column above its bottom interior portion; wherein all downcoming liquid below the bottom of the packing in said at least one column is collected, segregated and converted into a liquid phase and a vapor phase; wherein the vapor phase is passed upwardly through that column for discharge as overhead; and wherein the liquid phase is passed downwardly into said bottom interior portion of that column for discharge from that column.

34. A process according to claim 28 wherein the bottom interior portion of at least two of said first separation column, said second separation column, and said finishing column each has a reduced diameter relative to the diameter of that respective column above its bottom interior portion; wherein all downcoming liquid below the bottom of the packing in that respective column is collected, segregated and converted into a liquid phase and a vapor phase; wherein the vapor phase is passed upwardly through that respective column for discharge as overhead; and wherein the liquid phase is passed downwardly into said bottom interior portion of that respective column for discharge from that respective column.

35. A process according to claim 28 wherein the respective bottom interior portions of said first separation column, said second separation column, and said finishing column each has a reduced diameter relative to the diameter of that respective column above its bottom interior portion; wherein all downcoming liquid below the bottom of the packing in that respective column is collected, segregated and converted individually into a liquid phase and a vapor phase; wherein the vapor phase is passed upwardly through that respective column for discharge as overhead; and wherein the liquid phase is passed downwardly into said bottom interior portion of that respective column for discharge from that respective column.

36. A process according to claim 28 wherein the respective bottom portions of said first separation column, of said second separation column and of said finishing column are all equipped, individually, with at least (i) an internal trap out tray having a plurality of apertures therein, the upper side of the tray having individual vapor chimneys surrounding said apertures, (ii) an internal baffled section, (iii) a reboiler, (iv) a liquid transfer line from said baffled section to said reboiler, (v) a reboiler outlet line, and (vi) a reduced diameter bottom portion, such that:

A) the trap out tray collects all downcoming liquid below the bottom of the packing in that column and transfers the collected liquid to the baffled section;

B) the baffled section segregates said transferred liquid in a zone lower than said trap out tray;

C) the outlet line carries the segregated liquid to the reboiler;

D) the reboiler partially vaporizes the segregated liquid to produce a vapor phase and a liquid phase; and E) the reboiler outlet line transmits said vapor phase and said liquid phase to a discharge location in that column below the trap out tray so that said vapor phase passes upwardly through the apertures and vapor chimneys, and thence up the column, and said liquid phase passes downwardly into the reduced diameter bottom portion for discharge from that column.

37. A process according to claim 28 wherein a liquid distributor is disposed horizontally between superposed beds of structured packing in said first separation column or in said second separation column or in said finishing column or in any two or all three of said columns, and wherein each liquid distributor is configured such that the liquid depth therein is no more than about 4 inches.

38. A process according to claim 28 wherein a liquid distributor is disposed horizontally between all superposed beds of structured packing in two of said columns, and wherein each liquid distributor is configured such that the liquid depth therein is no more than about 4 inches.

39. A process according to claim 28 wherein a liquid distributor is disposed horizontally between all superposed beds of structured packing in all three of said columns, and wherein each liquid distributor is configured such that the liquid depth therein is no more than about 4 inches.

40. A process according to claim 28 wherein purified styrene overhead from said finishing column is subjected to vacuum stripping to remove one or more residual lower boiling impurities from the purified styrene.

41. A process according to claim 28 wherein at least one of said columns is operated at a vapor loading in the range of about 90 to about 95% of maximum loading such that turbulence in the liquid film is maintained without the occurrence of flooding.

42. A process according to claim 28 wherein at least two of said columns are operated at the same or different vapor loadings in the range of about 90 to about 95% of maximum loading such that turbulence in the liquid film in at least said two columns is maintained without the occurrence of flooding.

43. A process according to claim 28 wherein all of said columns are operated at the same or different vapor loadings in the range of about 90 to about 95% of maximum loading such that turbulence in the liquid film in each of said columns is maintained without the occurrence of flooding.

44. A process according to claim 32 wherein the bottom interior portion of at least one of said first separation column, said second separation column, and said finishing column has a reduced diameter relative to the diameter of said at least one column above its bottom interior portion; wherein all downcoming liquid below the bottom of the packing in said at least one column is collected, segregated and converted into a liquid phase and a vapor phase; wherein the vapor phase is passed upwardly through that column for discharge as overhead; and wherein the liquid phase is passed downwardly into said bottom interior portion of that column for discharge from that column.

45. A process according to claim 32 wherein the bottom interior portion of at least two of said first separation column, said second separation column, and said finishing column each has a reduced diameter relative to the diameter of that respective column above its bottom interior portion; wherein all downcoming liquid below the bottom of the packing in that respective column is collected, segregated and converted into a liquid phase and a vapor phase; wherein the vapor phase is passed upwardly through that respective column for discharge as overhead; and wherein the liquid phase is passed downwardly into said bottom interior portion of that respective column for discharge from that respective column.

46. A process according to claim 32 wherein the respective bottom interior portions of said first separation column, said second separation column, and said finishing column each has a reduced diameter relative to the diameter of that respective column above its bottom interior portion; wherein all downcoming liquid below the bottom of the packing in that respective column is collected, segregated and converted individually into a liquid phase and a vapor phase; wherein the vapor phase is passed upwardly through that respective column for discharge as overhead; and wherein the liquid phase is passed downwardly into said bottom interior portion of that respective column for discharge from that respective column.

47. A process for the separation of purified vinylaromatic monomer from a liquid mixture comprising vinylaromatic monomer, polymerization inhibitor, and aromatic hydrocarbon components having boiling points higher than that of styrene, which process comprises continuously feeding said mixture to a packed distillation column operating under conditions effecting such separation, the average residence time of liquid, inhibitor-depleted vinylaromatic monomer distillate overhead inside said column being less than 60 seconds, and recovering purified vinylaromatic monomer as overhead from said column.

48. A process according to claim 47 wherein the total annual production capacity per square foot of cross section of said column is in the range of about 9000 metric tons to about 22,000 metric tons.

49. A process according to claim 47 wherein said column is operated at a reflux ratio in the range of about 1.1 to about 5 times the minimum reflux ratio for said column.

50. A process according to claim 49 wherein the total annual production capacity per square foot of cross section of said column is in the range of about 9000 metric tons to about 22,000 metric tons.

51. A process for the separation of ethylbenzene from a liquid mixture comprising ethylbenzene, styrene monomer, and polymerization inhibitor, which process comprises continuously feeding said mixture to a packed distillation column operating under conditions effecting such separation, the average residence time of liquid, inhibitor-depleted vinylaromatic monomer distillate overhead inside said column being less than 60 seconds, and the total annual production capacity per square foot of cross section of said column being in the range of about 2000 metric tons to about 6000 metric tons.

52. A process according to claim 51 wherein said column is operated at a reflux ratio in the range of about 1.1 to about 5 times the minimum reflux ratio for said column.

53. A process according to claim 51 wherein said column is operated at a pressure in the range of about 10 psia to about 20 psia.

54. A process according to claim 53 wherein said column is operated at a reflux ratio in the range of about 1.1 to about 5 times the minimum reflux ratio for said column.

55. A process for the separation of one or more hydrocarbons boiling at a temperature below that of ethylbenzene from a liquid mixture comprising ethylbenzene, styrene monomer, and said one or more hydrocarbons, which process comprises continuously feeding said mixture and polymerization inhibitor, to a packed distillation column operating under conditions effecting such separation, the average residence time of liquid, inhibitor-depleted vinylaromatic monomer distillate overhead inside said column being less than 60 seconds, and the total annual production capacity per square foot of cross section of said column being in the range of about 9000 metric tons to about 22,000 metric tons.

56. A process according to claim 55 wherein said column is operated at a reflux ratio in the range of about 1.1 to about 5 times the minimum reflux ratio for said column.

57. A process according to claim 55 wherein said column is operated at a pressure in the range of about 10 psia to about 20 psia.

58. A process according to claim 57 wherein said column is operated at a reflux ratio in the range of about 1.1 to about 5 times the minimum reflux ratio for said column.

59. A process for the separation of purified styrene from a reaction mixture resulting from the catalytic dehydrogenation of ethylbenzene, said mixture comprising styrene, ethylbenzene and at least one aromatic hydrocarbon having a boiling point lower than that of ethylbenzene, which process comprises continuously feeding said mixture together with inhibitor into the first of a train of three packed distillation columns whereby:
  a) in the first column aromatic hydrocarbon having a boiling point lower than that of ethylbenzene is distilled off as overhead and bottoms from the first column are continuously fed to the second column;
  b) in the second column ethylbenzene is distilled off as overhead and bottoms are continuously fed to the third column;
  c) in the third column purified styrene is distilled off as overhead and bottoms are continuously discharged therefrom;

such that the total average liquid retention time in the three columns for materials that pass through the three columns is no more than about 60 minutes and the average residence time of liquid, inhibitor-depleted vinylaromatic monomer distillate overhead inside at least one of the columns is less than 60 seconds.

60. A process according to claim 59 wherein the average liquid retention time in said first column is no more than about 6 minutes, wherein the average liquid retention time in said second column is no more than about 40 minutes, and wherein the average liquid retention time in said third column is no more than about 14 minutes.

61. A process according to claim 59 wherein the average liquid retention time in said first column is no more than about 3 minutes, wherein the average liquid retention time in said second column is no more than about 28 minutes, and wherein the average liquid retention time in said third column is no more than about 10 minutes.

62. A process for the separation of purified styrene from a reaction mixture resulting from the catalytic dehydrogenation of ethylbenzene, said mixture comprising styrene, ethylbenzene and at least one aromatic hydrocarbon having a boiling point lower than that of ethylbenzene, which process comprises continuously feeding said mixture together with inhibitor into the first of three packed distillation columns whereby:
   a) in the first column aromatic hydrocarbons, including ethylbenzene, having boiling points lower than that of styrene are distilled off as overhead and fed to a second column, and bottoms from the first column are continuously fed to the third column;
   b) in the second column the aromatic hydrocarbons having boiling points below that of ethylbenzene are distilled off as overhead and the bottoms as taken off are principally ethylbenzene;
   c) in the third column purified styrene is distilled off as overhead and bottoms are continuously discharged therefrom;

such that the total average liquid retention time in the three columns for materials that pass through the three columns is no more than about 60 minutes and the average residence time of liquid, inhibitor-depleted vinylaromatic monomer distillate overhead inside at least one of the columns is less than 60 seconds.

63. A process according to claim 62 wherein the average liquid retention time in said first column is no more than about 40 minutes, wherein the average liquid retention time in said second column is no more than about 6 minutes, and wherein the average liquid retention time in said third column is no more than about 14 minutes.

64. A process according to claim 62 wherein the average liquid retention time in said first column is no more than about 28 minutes, wherein the average liquid retention time in said second column is no more than about 3 minutes, and wherein the average liquid retention time in said third column is no more than about 10 minutes.

* * * * *